United States Patent
Lawendy et al.

(10) Patent No.: US 9,421,222 B2
(45) Date of Patent: Aug. 23, 2016

(54) TREATMENT OF COMPARTMENT SYNDROME

(71) Applicant: LONDON HEALTH SCIENCES CENTRE RESEARCH INC., London (CA)

(72) Inventors: Abdel-Rahman Lawendy, London (CA); David W. Sanders, London (CA); Gediminas Cepinskas, London (CA)

(*) Notice: Subject to any disclaimer, the term of this patent is extended or adjusted under 35 U.S.C. 154(b) by 0 days.

(21) Appl. No.: 14/253,750

(22) Filed: Apr. 15, 2014

(65) Prior Publication Data
US 2014/0314879 A1    Oct. 23, 2014

Related U.S. Application Data

(60) Provisional application No. 61/812,072, filed on Apr. 15, 2013.

(51) Int. Cl.
*A61K 33/00* (2006.01)
*A61K 33/28* (2006.01)
*A61K 31/28* (2006.01)

(52) U.S. Cl.
CPC ............... *A61K 33/00* (2013.01); *A61K 31/28* (2013.01)

(58) Field of Classification Search
None
See application file for complete search history.

(56) References Cited

PUBLICATIONS

Guo et al.; American Journal of Physiology—Heart and Circulatory Physiology Published May 1, 2004 vol. 286 No. 5, H1649-H1653.*
Vera et al.; J Am Soc Nephrol; 16: 950-958, 2005.*
Lawendy et al.; J. Orthop Trauma; vol. 28; No. 11; Nov. 2014.*
Conrad MF, Stone DH, Alabadawi H, Hua HT, Entabi F, Stoner MC, Watkins MT. Local inflammatory and thrombotic responses differ in a murine model of partial and complete hindlimb ischemia/reperfusion. Surgery, 2005, p. 375-81, 138.
Matsen, F.A. 3rd, Compartmental syndromes, Hospital Practice, 1980, p. 113-117, 15.
Mubarak, S.J., Owen, C.A., Hargens, A.R., et al. Acute compartment syndromes: diagnosis and treatment with the aid of the wick catheter. The Journal of Bone and Joint Surgery. American vol. 60, 1091-1095 (1978).
Whitesides, T.E., Haney, T.C., Morimoto, K. et al. Tissue pressure measurements as a determinant for the need of fasciotomy. Clinical Orthopaedics and Related Research, 1975, p. 43-51.
Matsen, F.A., 3rd. Compartmental syndrome. An unified concept. Clinical Orthopaedics and Related Research, 1975, p. 8-14.
Rorabeck, C.H. & Clarke, K.M. The pathophysiology of the anterior tibial compartment syndrome: an experimental investigation. The Journal of Trauma,1978, p. 299-304, 18.
Hartsock, L.A., O'Farrell, D., Seaber, A.V. et al. Effect of increased compartment pressure on the microcirculation of skeletal muscle. Microsurgery, 1998, p. 67-71, 18.
Matsen, F.A., 3rd, Winquist, R.A. & Krugmire, R.B., Jr. Diagnosis and management of compartmental syndromes. The Journal of Bone and Joint Surgery, 1980, p. 286-291, American vol. 62.
Sheridan, G.W. & Matsen, F.A. An animal model of the compartmental syndrome. Clinical Orthopaedics and Related Research, 1975, p. 36-42.

(Continued)

*Primary Examiner* — Jeffrey T Palenik
(74) *Attorney, Agent, or Firm* — Eduardo Krupnik; Mller Thomson LLP

(57) ABSTRACT

The present invention relates to a method of treating or preventing compartment syndrome in a patient. According to the invention, the method includes: (a) identifying a patient suffering from compartment syndrome; and (b) administering to the patient a therapeutically effective amount of a carbon monoxide (CO).

30 Claims, 20 Drawing Sheets

(56) References Cited

PUBLICATIONS

Lawendy, A.R., Bihari, A., Sanders, D.W., et al. Compartment syndrome-induced microvascular dysfunction: an experimental rodent model. Canadian Journal of Surgery, 2011, p. 194-200, 54.

Sadasivan, K.K., Carden, D.L., Moore, M.B., et al. Neutrophil mediated microvascular injury in acute, experimental compartment syndrome. Clinical Orthopaedics and Related Research, 1997, p. 206-215.

Kalns, J., Cox, J., Baskin, J., et al. Threshold model for extremity compartment syndrome in swine. Journal of Surgical Research, 2011, e13-19, 167.

Ott, M.C., Scott, J.R., Bihari, A., et al. Inhalation of carbon monoxide prevents liver injury and inflammation following hind limb ischemia/reperfusion. The FASEB Journal, 2005, p. 106-108, 19.

Scott, J.R., Cukiemik, M.A., Ott, M.C., et al. Low-dose inhaled carbon monoxide attenuates the remote intestinal inflammatory response elicited by hindlimb ischemia-reperfusion. American Journal of Physiology. Gastrointestinal and Liver Physiology, 2009, p. G9-G14, 296.

Hegazi, R.A., Rao, K.N., Mayle, A., et al. Carbon monoxide ameliorates chronic murine colitis through a heme oxygenase 1-dependent pathway. Journal of Experimental Medicine, 2005, p. 1703-1713, 202.

Nakao, A., Kimizuka, K., Stolz, D.B., et al. Carbon monoxide inhalation protects rat intestinal grafts from ischemia/reperfusion injury. American Journal of Pathology, 2003, p. 1587-1598, 163.

Mazzola, S., Forni, M., Albertini, M., et al. Carbon monoxide pretreatment prevents respiratory derangement and ameliorates hyperacute endotoxic shock in pigs. FASEB Journal, 2005, p. 2045-2047, 19.

Motterlini, R. & Otterbein, L.E. The therapeutic potential of carbon monoxide. Nature Review Drug Discovery, 2010, p. 728-746, 9.

Motterlini, R. Carbon monoxide-releasing molecules (CO-RMs): vasodilatory, anti-ischaemic and anti-inflammatory activities. Biochemical Society Transactions, 2007, p. 1142-1146, 35.

Motterlini, R., Clark, J.E., Foresti, R., et al. Carbon monoxide-releasing molecules: characterization of biochemical and vascular activities. Circulation Research, 2002, p. E17-24, 90.

Cepinskas, G., Katada, K., Bihari, K., et al. Carbon monoxide liberated from carbon monoxide-releasing molecule CORM-2 attenuates inflammation in the liver of septic mice. American Journal of Physiology. Gastrointestinal and Liver Physiology, 2008, p. G184-191, 294.

Katada, K., Bihari, A., Mizuguchi, S., et al. Carbon monoxide liberated from CO-releasing molecule (CORM-2) attenuates ischemia/reperfusion (I/R)-induced inflammation in the small intestine. Inflammation, 2010, p. 92-100, 33.

Mizuguchi, S., Stephen, J., Bihari, A., et al. CORM-3-derived CO modulates polymorphonuclear leukocyte migration across the vascular endothelium by reducing levels of cell surface-bound elastase. American journal of physiology. Heart and Circulatory Physiology, 2009, p. H920-929, 297.

Clark, J.E., Naughton, P., Shurey, S., et al. Cardioprotective actions by a water-soluble carbon monoxide-releasing molecule. Circulation Research, 2003, pe2-8, 93.

Olson, S.A. & Glasgow, R.R. Acute compartment syndrome in lower extremity musculoskeletal trauma. Journal of American Academy of Orthopaedic Surgeons, 2005, p. 436-444, 13.

Santos-Silva, T., Mukhopadhyay, A., Seixas, J.D., et al. CORM-3 reactivity toward proteins: the crystal structure of a Ru(II) dicarbonyl-lysozyme complex. Journal of American Chemical Society, 2011, p. 1192-1195, 133.

Vadori, M., Seveso M., Besenzon, F., et al. In vitro and in vivo effects of the carbon monoxide-releasing molecule, CORM-3, in the xenogeneic pig-to-primate context. Xenotransplantation, 2009, p. 99-114, 16.

Katada, K., Bihari, A., Badhwar, A., et al. Hindlimb ischemia/reperfusion-induced remote injury to the small intestine: role of inducible nitric-oxide synthase-derived nitric oxide. The Journal of Pharmacology and Experimental Therapeutics, 2009, p. 919-927, 329.

Otterbein, L.E. The evolution of carbon monoxide into medicine. Respiratory Care, 2009, p. 925-932, 54.

Forbes, T.L., Carson, M., Harris, K.A., et al. Skeletal muscle injury induced by ischemia-reperfusion. Canadian Journal of Surgery, 1995, p. 56-63, 38.

Gute, D.C., Ishida, T., Yarimizu, K., et al. Inflammatory responses to ischemia and reperfusion in skeletal muscle. Molecular and Cellular Biochemistry, 1998, p. 169-187, 179.

Kurose, I., Anderson, D.C., Miyasaka, M., et al. Molecular determinants of reperfusion-induced leukocyte adhesion and vascular protein leakage. Circulation Research, 1994, p. 336-343, 74.

Forbes, T.L., Harris, K.A., Jamieson, W.G., et al. Leukocyte activity and tissue injury following ischemia-reperfusion in skeletal muscle. Microvascular Research, 1996, p. 275-287, 51.

Mizuguchi, S., Capretta, A., Suehiro, S., et al. Carbon monoxide-releasing molecule CORM-3 suppresses vascular endothelial cell SOD-1/SOD-2 activity while up-regulating the cell surface levels of SOD-3 in a heparin-dependent manner. Free Radical Biology & Medicine, 2010, p. 1534-1541, 49.

Song, H., Bergtrasser, C., Rafat, N., et al. The carbon monoxide releasing molecule (CORM-3) inhibits expression of vascular cell adhesion molecule-1 and E-selectin independently of haem oxygenase-1 expression. British Journal of Pharmacology, 2009, p. 769-780, 157.

Bergtraesser, C., Hoeger, S., Song, H., et al. Inhibition of VCAM-1 expression in endothelial cells by CORM-3: the role of the ubiquitin-proteasome system, p38, and mitochondrial respiration. Free Radical Biology and Medicine, 2012, p. 794-802, 52.

Ley, K., Laudanna, C., Cybulsky, M.I., et al. Getting to the site of inflammation: the leukocyte adhesion cascade updated. Nature Review Immunology, 2007, p. 678-689, 7.

Lancel, S., Hassoun, S.M., Favory, R., et al. Carbon monoxide rescues mice from lethal sepsis by supporting mitochondrial energetic metabolism and activating mitochondrial biogenesis. Journal of Pharmacology and Experimental Therapeutics, 2009, p. 641-648, 329.

Foresti, R., Hammad, J., Clark, J.E., et al. Vasoactive properties of CORM-3, a novel water-soluble carbon monoxide-releasing molecule. British Journal of Pharmacology, 2004, p. 453-460, 142.

Sabido F, Milazzo VJ, Hobson RW, 2nd and Duran WN. Skeletal muscle ischemia-reperfusion injury: a review of endothelial cell-leukocyte interactions. J Invest Surg, 1994, p. 39-47, 7(1).

Kurose I, Argenbright LW, Wolf R, Lianxi L and Granger DN. Ischemia/reperfusion-induced microvascular dysfunction: role of oxidants and lipid mediators. Am J Physiol, 1997, p. H2976-2982, 272(6 Pt 2).

Seddon HJ. Volkmann's ischaemia in the lower limb. J Bone Joint Surg Br, 1996, p. 627-636, 48(4).

Potter RF, Dietrich HH, Tyml K, Ellis CG, Cronkwright J, Groom AC. Ischemia-reperfusion induced microvascular dysfunction in skeletal muscle: application of intravital video microscopy. Int J Microcirc Clin Exp., 1993, p. 173-186, 13.

Tyml K, Budreau CH. A new preparation of rat extensor digitorum longus muscle for intravital investigation of the microurculation. Int J Microcirc Clin Exp., 1991, p. 335-343, 10(4).

Potter RF, Peters G, Carson M, Forbes T, Ellis CG, Harris KA, Derose G, Jamieson WG. Measurement of tissue viability using intravital microscopy and fluorescent nuclear dyes. J Surg Res., 1995, p. 521-526, 59(5).

Brock RW, Carson MW, Harris KA, Potter RF. Microcirculatory perfusion deficits are not essential for remote parenchymal injury within the liver. Am J Physiol., 1999, p. G55-60, 277(1 Pt 1).

Campbell JJ, Hedrick J, Zlotnik A, Siana MA, Thompson DA, Butcher EC. Chemokines and the arrest of the lymphocytes rolling under flow conditions. Science, 1998, p. 381-384, 279.

(56) References Cited

OTHER PUBLICATIONS

Schlag G, Harris KA, Potter RF. Role of leukocyte accumulation and oxygen radicals in ischemia-reperfusion-induced injury in skeletal muscle. Am J Physio Heart Circ Physiol. 2001, p. H1716-21, 280(4).
Heppenstalli RB, Scott R, Sapega, A, Park YS, Chance B. A comparative study of the tolerance of skeletal muscle to ischemia. Tourniquet application compared with acute compartment syndrome. J Bone and Joint Surg., 1986, p. 820-823, 68-A.

Matsen FA III, Mayo KA, Krugmire RB, Sheridan GW, Kraft GH. A model compartmental syndrome in man with particular reference to the quantification of nerve function. J Bone and Joint Surg., 1977, p. 648-653, 59-A.
Sheridan GW, Matsen FA, Krugmire RB Jr. Further investigation on the pathophysiology of the compartment syndrome . Clin Orthop. 1977, p. 266-267, 123.

* cited by examiner

TREATMENT OF COMPARTMENT SYNDROME

FIELD OF THE INVENTION

The present invention relates to compartment syndrome. More particularly, the present invention relates to methods of preventing, treating and delaying the effects of compartment syndrome in the limbs of a patient using carbon monoxide.

BACKGROUND OF THE INVENTION

Acute limb compartment syndrome (CS), a potentially devastating complication of musculoskeletal trauma, is characterized by an increase in pressure within a closed osseofascial compartment, resulting in muscle-threatening and ultimately limb-threatening ischemia. [1-6] The fascia, unlike other body tissues, are unable to expand Fasciotomy, to fully decompress all the muscles in the involved compartments, remains the only effective treatment and current gold-standard surgical therapy. Despite a large body of literature dedicated to understanding the pathophysiology of CS, the mechanisms of CS-induced tissue damage are rather poorly understood.

Extremity CS occurs once swelling within a muscle compartment develops to such a degree that the tissue perfusion becomes compromised. The established view of the pathophysiological process of CS development is that increasing compartmental pressure compromises microcirculatory perfusion, thus restricting oxygen and nutrient delivery to vital tissues, ultimately resulting in cellular anoxia and severe tissue necrosis. [3,5,7,8] Unlike complete ischemia, CS causes myonecrosis in the face of patent vessels.

Surgery is needed immediately. A delay in relieving the mounting pressure within the fascia (measured sometimes in a delay as short as a few hours) will result in a permanent damage to delicate structures such as nerves and muscles and extensive propagation of tissues necrosis. Slowing of nerve conduction may occur after 2 hours of compression, neuropraxia after 3 to 4 hours, variable muscle tissue damage after 6 hours, and irreversible muscle tissue changes and irreversible changes to the nerves may include after 8 hours of tissue compression. In more severe cases, amputation may be required.

There is probably no way to prevent this condition. However, with prompt diagnosis and treatment, the prognosis is excellent for recovery of the muscles and nerves inside the compartment.

In view of the foregoing, the current surgical gold standard in CS diagnosis dictates that surgical fasciotomy must be performed within 6 hours to avoid permanent tissue damage.

Carbon monoxide (CO) gas is poisonous in high concentrations. However, it is now recognized that inhalation of low levels of carbon monoxide have anti-inflammatory effects in some models and to offer protection to microvascular perfusion. [12-16] Although the exogenous administration of CO via inhalation (250 ppm) has been shown beneficial during systemic inflammatory response syndrome [12,13], such method of administration results in increased carboxyhemoglobin (COHb) levels, thus presenting a potential threat to the host.

Carbon monoxide has been disclosed in U.S. Pat. No. 7,678,390 as a biomarker and therapeutic agent of heart, lung, liver, spleen, brain, skin and kidney diseases and other conditions and disease states including, for example, asthma, emphysema, bronchitis, adult respiratory distress syndrome, sepsis, cystic fibrosis, pneumonia, interstitial lung diseases, idiopathic pulmonary diseases, other lung diseases including primary pulmonary hypertension, secondary pulmonary hypertension, cancers, including lung, larynx and throat cancer, arthritis, wound healing, Parkinson's disease, Alzheimer's disease, peripheral vascular disease and pulmonary vascular thrombotic diseases such as pulmonary embolism. U.S. Pat. No. 7,687,079 discloses CO in the treatment of ileus. However, CO has never been suggested for the treatment of CS.

Transitional metal carbonyls, CO-releasing molecules (CO-RMs) have been used to deliver CO in a controlled manner without significantly altering COHb. [18, 19, 23] The major advantage of using CO-RMs versus inhaled CO is the ability to control CO delivery without significantly increasing COHb, and choice of various routes (intravenous, intraperitoneal, subcutaneous or tissue superfusion) of CO administration to target specific organs/tissues. Consequently, CO-RMs have received an increased attention for the potential pharmaceutical application. [17-19] CO-RMs have been shown to act pharmacologically in rat aortic and cardiac tissue, where liberation of CO produced vasorelaxant effects, decreased myocardial ischemia/reperfusion damage, and reduced inflammatory response in LPS-stimulated macrophages. [20-23]

U.S. Pat. No. 8,697,747 discloses the use of CORM for controlling bleeding (e.g., enhancing coagulation and reducing fibrinolysis). This patent, however, does not disclose, teach or suggest the use of CORM in the treatment, prevention or prophylaxis of CS. Furthermore, this patent shows that both inactive and active forms of CORM-2 enhanced coagulation and reduced fibrinolysis (see Examples 1 and 2), indicating that it is the CORM molecule itself the principal active agent and not the CO. Clotting cascade is not relevant to the topic of compartment syndrome.

In view of the foregoing there is a need to decrease the morbidity associated with CS and expand the surgical window by preserving the muscle tissue and its function.

An object of the present invention is to develop a method of treating CS, which would reduce the morbidity and disability in patients.

SUMMARY OF THE INVENTION

The present invention is based, in part, on the discovery that administration of carbon monoxide (CO) can attenuate and treat compartment syndrome.

In one embodiment, the present invention is a method for treating or relieving compartment syndrome in a patient. In one embodiment, the method includes: administering to the patient a therapeutically effective amount of a CO.

In one embodiment of the method of treating compartment syndrome, the CO is provided as a gaseous composition comprising CO and at least one other gaseous molecule.

In another embodiment the carbon monoxide (CO) is provided in CO-releasing molecules (CORM).

In another embodiment, the CORM is CORM-3 (tricarbonylchloro-glycinate-ruthenium (II)).

In another embodiment, the CORM-3 is provided as a single dose or multiple dosages, each dose comprising about 10 mg of CORM per kg of the patient.

In another embodiment, the CORM is selected from the group consisting of tricarbonyldichloro ruthenium (II) dimer, sodium boranocarbonate, dimanganese decacarbonyl, and iron pentacarbonyl.

In another embodiment of the method of the present invention the CO is provided from about 50 ppm to about 500 ppm.

In another embodiment of the method of the present invention, the carbon monoxide is administered before, after or during the patient undergoing fasciotomy.

In one embodiment of the present invention, the compartment syndrome is in a limb of the patient.

In one embodiment, the present invention provides for a method for the prevention of elevated compartment pressure in a patient comprising administering to the patient carbon monoxide (CO) in an amount sufficient to decrease compartment pressure.

In another embodiment, the present invention provides for a method of treating a subject at risk of developing compartment syndrome. The method, in one embodiment, includes administering to the subject a therapeutically effective amount of carbon monoxide (CO).

The present invention relates also to CO for use in the treatment or relieving of compartment syndrome, for use in preventing elevated compartment pressure in a patient, and for use in treating a subject at risk of developing compartment syndrome.

Further and other objects of the invention will be realized from the following Summary of the Invention, the Discussion of the Invention and the embodiments and Examples thereof.

BRIEF DESCRIPTION OF THE DRAWINGS

Embodiments will now be described, by way of example only, with reference to the drawings, in which.

DETAILED DESCRIPTION OF THE INVENTION

Definitions

Figure 1:
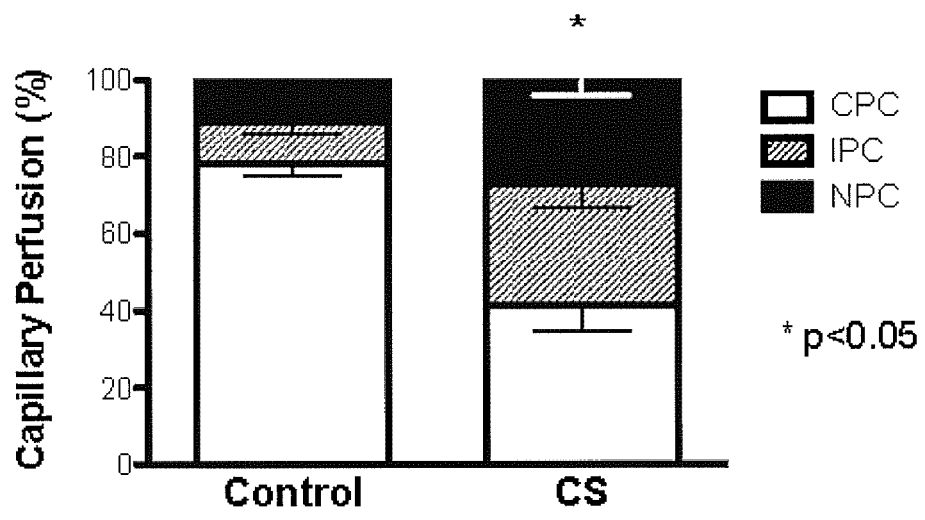
FIG. 1 is a graph illustrating the effect of elevated intra-compartmental pressure on microvascular perfusion measured using intravital videomicroscopy ($p<0.05$). N=5 in each group. CS, compartment syndrome; CPC, continuously-perfused capillaries; IPC, intermittently-perfused capillaries; NPC, non-perfused capillaries.

In this specification and in the claims that follow, reference will be made to a number of terms that shall be defined to have the meanings below. All numerical designations, e.g., dimensions and weight, including ranges, are approximations that typically may be varied (+) or (−) by increments of 0.1, 1.0, or 10.0, as appropriate. All numerical designations may be understood as preceded by the term "about".

Non-limiting terms are not to be construed as limiting unless expressly stated or the context clearly indicates otherwise (for example "including", "having" and "comprising" typically indicate "including without limitation"). The singular form "a", "an", and "the" includes plural references unless the context clearly dictates otherwise. The priority document as well as all documents cited, are incorporated by reference.

The term "carbon monoxide" ("CO") as used herein describes molecular carbon monoxide in its gaseous state, compressed into liquid form, or dissolved in aqueous solution. The term "carbon monoxide composition" or "pharmaceutical composition comprising carbon monoxide" is used throughout the specification to describe a gaseous or liquid composition containing carbon monoxide that can be administered to a patient and/or an organ. The person of ordinary skill in the art will recognize which form of the pharmaceutical composition, e.g., gaseous, liquid, or both gaseous and liquid forms, is preferred for a given application.

The terms "effective amount" and "effective to treat," as used herein, refer to the administration of carbon monoxide in an amount or concentration and for period of time including acute or chronic administration and periodic or continuous administration that is effective within the context of its administration for causing an intended effect or physiological outcome. Effective amounts of CO for use in the present invention include, for example, amounts that may prevent or reduce the morbidity and disability in patients having CS.

For gases, effective amounts of CO generally fall within the range of about 0.0000001% to about 0.3% by weight, e.g., 0.0001% to about 0.25% by weight, preferably at least about 0.001%, e.g., at least about 0.005%, 0.010%, 0.02%, 0.025%, 0.03%, 0.04%, 0.05%, 0.06%, 0.08%, 0.10%, 0.15%, 0.20%, 0.22%, or 0.24% by weight CO. For liquid solutions of CO, effective amounts generally fall within the range of about 0.0001 to about 0.0044 g CO/100 g liquid, e.g., at least about 0.0001, 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. A person of ordinary skill in the art will appreciate that amounts outside of these ranges may be used depending upon the application.

The term "patient" is used throughout the specification to describe an animal, human or non-human, to whom treatment according to the methods of the present invention is provided. Veterinary applications are clearly anticipated by the present invention. The term includes but is not limited to mammals, e.g., humans, other primates, pigs, rodents such as mice and rats, rabbits, guinea pigs, hamsters, cows, horses, cats, dogs, sheep and goats. The term "treat(ment)," is used herein to describe delaying the onset of, inhibiting, preventing, or alleviating the effects, morbidity and disability of compartment syndrome.

Individuals considered at risk for developing compartment syndrome may benefit particularly from the invention, primarily because surgery can begin before there is any irreversible damage to muscle and nerve tissues. Individuals "at risk" include, e.g., individuals having an increased risk of trauma, including acute trauma, on the limbs, such as soldiers, athletes, individuals that were involved in car accidents, and so forth. The skilled practitioner will appreciate that a patient can be determined to be at risk for CS by any method known in the art, e.g., by a physician's diagnosis.

Preparation of Gaseous Compositions

A CO composition may be a gaseous carbon monoxide composition. Compressed or pressurized gas useful in the methods of the invention can be obtained from any commercial source, and in any type of vessel appropriate for storing compressed gas. For example, compressed or pressurized gases can be obtained from any source that supplies compressed gases, such as oxygen, for medical use. The term "medical grade" gas, as used herein, refers to gas suitable for administration to patients as defined herein. The pressurized gas including carbon monoxide used in the methods of the present invention can be provided such that all gases of the desired final composition (e.g., CO, He, NO, CO2, O2, N2) are in the same vessel, except that NO and O2 cannot be stored together. Optionally, the methods of the present invention can be performed using multiple vessels containing individual gases. For example, a single vessel can be provided that contains carbon monoxide, with or without other gases, the contents of which can be optionally mixed with room air or with the contents of other vessels, e.g., vessels containing oxygen, nitrogen, carbon dioxide, compressed air, or any other suitable gas or mixtures thereof.

Gaseous compositions administered to a patient according to the present invention typically contain 0% to about 79% by weight nitrogen, about 21% to about 100% by weight oxygen and about 0.0000001% to about 0.3% by weight (corresponding to about 1 ppb or 0.001 ppm to about 3,000 ppm) carbon monoxide. Preferably, the amount of nitrogen in the gaseous composition is about 79% by weight, the amount of oxygen is about 21% by weight, and the amount of carbon monoxide is about 0.0001% to about 0.25% by weight. The amount of CO is preferably at least about 0.001%, e.g., at least about 0.005%, 0.010%, 0.02%, 0.025%, 0.03%, 0.04%, 0.05%, 0.06%, 0.08%, 0.10%, 0.15%, 0.20%, 0.22%, or 0.24% by weight. Preferred ranges include about 0.005% to about 0.24%, about 0.01% to about 0.22%, about 0.015% to about 0.20%, about 0.08% to about 0.20%, and about 0.025% to about 0.1% by weight. It is noted that gaseous carbon monoxide compositions having concentrations of carbon monoxide greater than 0.3% (such as 1% or greater) may be used for short periods (e.g., one or a few breaths), depending upon the application.

A gaseous carbon monoxide composition may be used to create an atmosphere that comprises carbon monoxide gas. An atmosphere that includes appropriate levels of carbon monoxide gas can be created, for example, by providing a vessel containing a pressurized gas comprising carbon monoxide gas, and releasing the pressurized gas from the vessel into a chamber or space to form an atmosphere that includes the carbon monoxide gas inside the chamber or space. Alternatively, the gases can be released into an apparatus that culminates in a breathing mask or breathing tube, thereby creating an atmosphere comprising carbon monoxide gas in the breathing mask or breathing tube, ensuring the patient is the only person in the room exposed to significant levels of carbon monoxide.

Carbon monoxide levels in an atmosphere can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026-2032, 1982; Ingi et al., Neuron 16:835-842, 1996). Sub-parts per million carbon monoxide levels can be detected by, e.g., gas chromatography and radioisotope counting. Further, it is known in the art that carbon monoxide levels in the sub-ppm range can be measured in biological tissue by a midinfrared gas sensor (see, e.g., Morimoto et al., Am. J. Physiol. Heart. Circ. Physiol 280:H482-H488, 2001). Carbon monoxide sensors and gas detection devices are widely available from many commercial sources.

Preparation of Liquid Compositions

A carbon monoxide composition may also be a liquid carbon monoxide composition. A liquid can be made into a carbon monoxide composition by any method known in the art for causing gases to become dissolved in liquids. For example, the liquid can be placed in a so-called "CO2 incubator" and exposed to a continuous flow of carbon monoxide, preferably balanced with carbon dioxide, until a desired concentration of carbon monoxide is reached in the liquid. As another example, carbon monoxide gas can be "bubbled" directly into the liquid until the desired concentration of carbon monoxide in the liquid is reached. The amount of carbon monoxide that can be dissolved in a given aqueous solution increases with decreasing temperature. As still another example, an appropriate liquid may be passed through tubing that allows gas diffusion, where the tubing runs through an atmosphere comprising carbon monoxide (e.g., utilizing a device such as an extracorporeal membrane oxygenator). The carbon monoxide diffuses into the liquid to create a liquid carbon monoxide composition.

It is likely that such a liquid composition intended to be introduced into a living animal will be at or about 37° C. at the time it is introduced into the animal.

The liquid can be any liquid known to those of skill in the art to be suitable for administration to patients. In general, the liquid will be an aqueous solution. Examples of appropriate solutions include Phosphate Buffered Saline (PBS), Celsior™, Perfadex™ Collins solution, citrate solution, and University of Wisconsin (UW) solution. In one embodiment of the present invention, the liquid is Ringer's Solution, e.g., lactated Ringer's Solution, or any other liquid that can be used infused into a patient. In another embodiment, the liquid includes blood, e.g., whole blood.

Any suitable liquid can be saturated to a set concentration of carbon monoxide via gas diffusers. Alternatively, premade solutions that have been quality controlled to contain set levels of carbon monoxide can be used. Accurate control of dose can be achieved via measurements with a gas permeable, liquid impermeable membrane connected to a carbon monoxide analyzer. Solutions can be saturated to desired effective concentrations and maintained at these levels.

Treatment of Patients with Carbon Monoxide Compositions

A patient at risk of developing CS can be treated with a carbon monoxide composition by any method known in the art of administering gases and/or liquids to patient. Carbon monoxide compositions can be administered to a patient diagnosed with, or determined to be at risk for CS. The invention contemplates the systemic administration of liquid or gaseous carbon monoxide compositions to patients (e.g., by inhalation and/or ingestion), the injection of the compositions to the patients (e.g. by injection to the intraperitoneal cavity), and the topical administration of the compositions to the patient's exposed/affected compartment(s).

Systemic Delivery of Carbon Monoxide

Gaseous carbon monoxide compositions can be delivered systemically to a patient. Gaseous carbon monoxide compositions are typically administered by inhalation through the mouth or nasal passages to the lungs, where the carbon monoxide may be readily absorbed into the patient's bloodstream. The concentration of active compound (CO) utilized in the therapeutic gaseous composition will depend on absorption, distribution, inactivation, and excretion (generally, through respiration) rates of the carbon monoxide as well as other factors known to those of skill in the art. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. Acute, sub-acute and chronic administration of carbon monoxide are contemplated by the present invention, depending upon, e.g., the severity of the trauma in the patient. Carbon monoxide can be delivered to the patient for a time (including indefinitely) sufficient to treat the condition and exert the intended pharmacological or biological effect.

The following are examples of some methods and devices that can be utilized to administer gaseous carbon monoxide compositions to patients.

Ventilators

Medical grade carbon monoxide (concentrations can vary) can be purchased mixed with air or another oxygen-containing gas in a standard tank of compressed gas (e.g., 21% 02, 79% N2). It is non-reactive, and the concentrations that are required for the methods of the present invention are well below the combustible range (10% in air). In a hospital setting, the gas presumably will be delivered to the bedside where it will be mixed with oxygen or house air in a blender to a desired concentration in ppm (parts per million). The patient will inhale the gas mixture through a ventilator, which will be set to a flow rate based on patient comfort and needs. This is determined by pulmonary graphics (i.e., respiratory rate, tidal volumes etc.). Fail-safe mechanism(s) to prevent the patient from unnecessarily receiving greater than desired amounts of carbon monoxide can be designed into the delivery system. The patient's carbon monoxide level can be monitored by studying (1) carboxyhemoglobin (COHb), which can be measured in venous blood, and (2) exhaled carbon monoxide collected from a side port of the ventilator. Carbon monoxide exposure can be adjusted based upon the patient's health status and on the basis of the markers. If necessary, carbon monoxide can be washed out of the patient by switching to 100% O2 inhalation. Carbon monoxide is not metabolized; thus, whatever is inhaled will ultimately be exhaled except for a very small percentage that is converted to CO2. Carbon monoxide can also be mixed with any level of O2 to provide therapeutic delivery of carbon monoxide without consequential hypoxic conditions.

Face Mask and Tent

A carbon monoxide-containing gas mixture is prepared as above to allow passive inhalation by the patient using a face-mask or tent. The concentration inhaled can be changed and can be washed out by simply switching over to 100% O2. Monitoring of carbon monoxide levels would occur at or near the mask or tent with a fail-safe mechanism that would prevent too high of a concentration of carbon monoxide from being inhaled.

Portable Inhaler

Compressed carbon monoxide can be packaged into a portable inhaler device and inhaled in a metered dose, for example, to permit intermittent treatment of a recipient who is not in a hospital setting. Different concentrations of carbon monoxide could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung

An artificial lung (a catheter device for gas exchange in the blood) designed for $O_2$ delivery and $CO_2$ removal can be used for carbon monoxide delivery. The catheter, when implanted, resides in one of the large veins and would be able to deliver carbon monoxide at given concentrations either for systemic delivery or at a local site. The delivery can be a local delivery of a high concentration of carbon monoxide for a short period of time at the site of the trauma, e.g., in proximity to the site of trauma or affected compartment(s) (this high concentration would rapidly be diluted out in the bloodstream), or a relatively longer exposure to a lower concentration of carbon monoxide (see, e.g., Nattier et al., Artif. Organs 18(11):806-812 (1994); and Golob et al., ASAIO J., 47(5):432-437 (2001)).

Normobaric Chamber

In certain instances, it would be desirable to expose the whole patient to carbon monoxide. The patient would be inside an airtight chamber that would be flooded with carbon monoxide (at a level that does not endanger the patient, or at a level that poses an acceptable risk without the risk of bystanders being exposed. Upon completion of the exposure, the chamber could be flushed with air (e.g., 21% 02, 79% N2) and samples could be analyzed by carbon monoxide analyzers to ensure no carbon monoxide remains before allowing the patient to exit the exposure system.

Systemic Delivery of Liquid CO Compositions

The present invention further contemplates that liquid CO compositions can be created for systemic delivery to a patient, e.g., by infusion into a patient. For example, liquid CO compositions, such as CO-saturated Ringer's Solution, can be infused into a patient before, during, and/or after fasciotomy. Alternatively or in addition, CO-partially or completely saturated whole (or partial) blood can be infused into the patient. The present invention also contemplates that agents capable of delivering doses of CO gas or liquid can be utilized (e.g., CO releasing gums, creams, ointments or patches).

Topical Treatment with Carbon Monoxide

Alternatively or in addition, carbon monoxide compositions can be applied directly to the site of the trauma, the affected compartment(s) or to any portion thereof. A gaseous composition can be directly applied to the affected compartment(s) of a patient during surgery.

CO may be sprayed on the site of the trauma or to the opened, affected compartment(s).

CO-Releasing Molecules

The present invention contemplates that compounds that release CO into the body after administration of the compound (e.g., CO-releasing compounds, e.g., photoactivatable CO-releasing compounds), e.g., dimanganese decacarbonyl, tricarbonylchloro(glycinato)ruthenium (II) (CORM-3), tricarbonyldichlororuthenium (II) dimer, sodium boranocarbonate, iron pentacarbony and methylene chloride, may also be used in the methods of the present invention, as can carboxyhemoglobin and CO-donating hemoglobin substitutes.

Transitional metal carbonyls, CO-releasing molecules (CORMs) have been used to deliver CO in a controlled manner without significantly altering COHb. [17] The major advantage of using CORMs versus inhaled CO is the ability to control CO delivery without significantly increasing COHb, and choice of various routes (intravenous, intraperitoneal, subcutaneous or tissue superfusion) of CO administration to target specific organs/tissues. Accordingly, the present application contemplates the use of CORMs in the treatment of CS.

Carbon monoxide releasing molecules (CORM) refers to a metal carbonyl compound or a pharmaceutically acceptable salt thereof that releases carbon monoxide. CORMs and pharmaceutically acceptable salts thereof suitable for the methods of the present invention may include those including a transition metal or metalloid and one or more carbonyl ligand(s). The transition metal or metalloid, for example, can be ruthenium, iron, manganese, cobalt, nickel, molybdenum, rhodium, or boron. The carbonyl ligand(s) may be coordinated to the metal center, or bonded to other groups by ionic or covalent bonds. The CORMs and pharmaceutically acceptable salts thereof for use with the methods of the present invention may also include additional ligands that may modulate a particular property of the CORM, such as, for example, the rate of releasing carbon monoxide, solubility, hydrophobicity, stability, or electrochemical potential. The additional ligands can be, for example, halides, sulfoxides, natural and synthetic amino acids, aromatics, carboxylates, ethers, alcohols, or nitriles. The CORM or a pharmaceutically acceptable salt thereof may also include a targeting moiety useful for facilitating release of carbon monoxide at an appropriate site. The targeting moiety can be, for example, capable of binding a receptor on a particular target cell surface to promote release of carbon monoxide at the required site.

The CO-releasing molecules described herein may be prepared in a variety of ways, such as the methods described in Motterlini, R. & Otterbein, L. E [17].

Synthetic methods for obtaining CO-releasing molecules are also described in U.S. Pat. No. 7,045,140. In the case of CO-RM-3, for example, $[Ru(CO)_3Cl_2]_2$ (0.129 g, 0.25 mmol) and glycine (0.039 g, 0.50 mmol) were placed under nitrogen in a round bottomed flask. Methanol (75 cm3) and sodium ethoxide (0.034 g, 0.50 mmol) were added and the reaction allowed to stir for 18 hours. The solvent was then removed under pressure and the yellow residue re-dissolved in THF, filtered and excess 40-60 light petroleum added. The yellow solution was evaporated down to give a pale yellow solid (0.142 g, 96%).

One or more of the compounds described herein or pharmaceutically acceptable salts thereof may be provided in a pharmaceutical composition. The pharmaceutical composition may be formulated in accordance with its use and mode of administration. The compositions will include a therapeutically effective amount of one or more of the compounds described herein or derivatives thereof in combination with a pharmaceutically acceptable carrier and, optionally, can further include other agents, including other therapeutic agents. These compositions can be prepared in any manner available in the art and can be administered in a number of ways depending on whether local or systemic treatment is desired, on the area to be treated, the subject to be treated, and other variables. Thus, the disclosed compositions and compounds can be administered, for example, orally, parenterally (e.g., intravenously), intraventricularly, intramuscularly, intraperitoneally, transdermally, extracorporeally, or topically. The compositions and compounds can be administered locally.

By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound described herein or pharmaceutically acceptable salts thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Administration of the CORMs described herein or pharmaceutically acceptable salts thereof may be carried out using therapeutically effective amounts of the CORMs described herein or pharmaceutically acceptable salts thereof for periods of time effective to treat or prevent compartment syndrome, or to extend the window for fasciotomy. For example, the CORMs described herein or pharmaceutically acceptable salts thereof can be administered as a single dose (i.e., bolus dosage) or as multiple doses. The effective amount of the CORMs described herein or pharmaceutically acceptable salts thereof can be determined by one of ordinary skill in the art and includes exemplary dosage amounts for a subject of from about 25 µM to about 200 µM of the CORM. Alternatively, the dosage amount may be 10 mg of CORM per kilogram of the subject or patient. Those of skill in the art will understand that the specific dose level and frequency of dosage for any particular subject will vary and will depend upon a variety of factors, including the metabolic stability and length of action of the CORM, the species, the mode and time of administration, the rate of excretion, drug combination, and the type and severity of the particular condition.

Administration any of the above can be administered to a patient in any way, e.g., by topical, oral, intravenous, or intraarterial administration. Any of the above compounds can be administered to the patient locally and/or systemically, and in any combination.

CORMs may be administered as a single dose or multiple dosages.

The invention is illustrated in part by the following examples, which are not to be taken as limiting the invention in any way.

Advantages

The current surgical gold standard in CS diagnosis dictates that surgical fasciotomy must be performed within 6 hours to avoid permanent tissue damage. The use of CO has the ability to expand the surgical window by preserving the muscle tissue and its function. Thus, any diagnosed CS (or any compartment at risk for developing CS or any person at risk of developing CS) may use this medical therapy to decrease the morbidity associated with the disease. Any subject having a compartment at risk may be treated by the methods of the present invention regardless of their need for enhanced coagulation or reduced fibrinolysis. The present invention relates to the treatment of compromised muscle as a result of increased pressure.

In order to aid in the understanding and preparation of the present invention, the following illustrative, non-limiting examples are provided.

EXAMPLES

Example 1

Experimental Rodent Model

Introduction

Acute limb compartment syndrome (CS) is characterized by raised pressure within a closed fascial compartment (1-4). Untreated it may lead to tissue necrosis and permanent functional impairment (3). The clinical sequelae of compartment syndrome, first described by Richard von Volkmann in 1875, relates irreversible contractures of the hand to an ischemic process in the forearm. Despite the breadth of research dedicated to understanding the pathophysiology of CS, the mechanisms causing the tissue and microvascular injury associated with acute compartment syndrome are complex and remain only partly understood. Factors hindering our understanding of CS pathophysiology include limitations in clinical trials due to the severe acuity of CS, absence of a clinically relevant standardized animal model and the difficulty of applying invasive tools to help delineate the pathways that propagate the CS injury at a cellular level.

Intravital video microscopy (IVVM) is a modern technique allowing for the visualization and study of microvascular perfusion (42). This technique has previously been used in the study of ischemia-reperfusion, ischemic preconditioning, sepsis and other disease states that may compromise blood flow (29, 42). The purpose of this study was to develop a clinically relevant small animal model of elevated intracompartmental pressure and to employ IVVM in order to study the microvascular and inflammatory response to compartment syndrome.

Methods

Animal Description and Care

Male Wistar rats utilized for these experiments had access to food and water ad libitum. All protocols and experiments were conducted in agreement with the Committee on the Care and Use of Laboratory Animals of the Institute of Laboratory Animals Resources, National Research Council, and approved by the institutional Council on Animal Care.

Experimental Protocol

Ten rats (175-250 g) were anesthetized with inhalational isoflurane. Following induction at 5% isoflurane in a 1:1 O2:N2 mixture, anaesthesia was maintained at 2% isoflurane and titrated to maintain general anesthesia. The carotid artery was cannulated for continuous blood pressure monitoring and fluid replacement to maintain a normal mean arterial pressure at 100 mmHg. Once anesthetized, compartment pressure was elevated by slowly infusing isotonic normal saline via a 24-gauge angiocatheter into the anterior compartment of the left hindlimb for the experimental group. Compartment pressure was raised to 30 mmHg and maintained between 30-40 mmHg for the duration of the protocol.

An electronic compartmental pressure monitoring system (Synthes USA, Paoli Pa.) was inserted into the anterior and then posterior compartment through a 14-gauge angiocatheter. As the pressure rose within the hindlimb, both the anterior and posterior compartments became isobaric (both anterior and posterior co mpartment pressures were raised to 30-40 mmHg). In order to test the effect of time on capillary perfusion and cellular injury, elevated intracompartmental pressure (EICP) was maintained for 45 min (n=5) prior to the release of the EICP via fasciotomy. Control animals (n=5) had all the same preparation, however no saline was infused into the compartment via the catheter and the intracompartmental pressure was held at control levels for the duration of the experiment prior to fasciotomy.

Surgical Technique

The Extensor Digitorum Longus (EDL) muscle was prepared for intravital microscopy, as previously described (42; 29, 43). In brief, the exposure of the EDL muscle began by incising the skin over the posterior aspect of the hindlimb. The underlying biceps femoris muscle was retracted to expose the tibialis anterior and the lateral gastrocnemius muscles. These muscles were divided to expose the EDL. The overlying fascia was incised. A suture ligature was applied around the distal tendon of the EDL. The tendon was then cut from its bony insertion to allow the EDL to be reflected onto the microscope stage with its proximal arterial and venous pedicle intact. Once prepared, animals were placed onto the stage of an inverted microscope (Nikon Diaphot 300) and the EDL was reflected onto a slide moistened with saline. A cover slip was placed on top of the EDL, and all exposed tissues were covered with a plastic film, to isolate the preparation from the atmosphere and to prevent drying. A heat lamp maintained the EDL muscle temperature (32° C.) as well as the core temperature (37° C.) of the rat. Care was taken to ensure that the time from fasciotomy to the first microscopy recording was no more than 5 minutes.

Intravital Microscopy and Video Analysis

The muscle preparations remained on the microscope with intact circulation post fasciotomy. Five fields of view within the EDL were randomly chosen containing a complete microvascular unit (arteriole, capillary bed, and post capillary venule). These fields were recorded onto video using a 20× objective, for a final magnification of 700× at the monitor. The microscope was connected to a charged-coupled device camera (Dage-MTI VE1000), a time-date generator (WJ-810, Panasonic), and a computer. Appropriate white light illumination was obtained using fiber-optic guides. One-minute video recording of each field of view was obtained post-fasciotomy and stored on the computer for later analysis. An additional 15 seconds was recorded for the nuclear dye staining. This period is limited to reduce exposure to excitation wavelength in order to preserve the fluorochrome contained within the dyes.

Perfusion Analysis

An index of compartment syndrome-induced microvascular dysfunction was determined by counting the number of perfused capillaries crossing three equidistant parallel lines drawn on the computer monitor, perpendicular to the capillary axis and expressed as the number of perfused capillaries by red blood cells per millimeter line length (Npc/mm) following our previously validated methodology (42; 29, 32).

Injury Analysis

Following fasciotomy, fluorescent vital dyes ethidium bromide (EB, 5 µg/mL) and bisbenzimide (BB, 5 µg/mL) were added to the saline bath as previously described (32; 44). The topical use of bisbenzimide and ethidium bromide does not alter microvascular perfusion and is a reliable technique for cellular labelling in the live animal (44). Bisbenzimide, a membrane-permeant dye, stains the nucleus of all cells. Ethidium bromide, a larger molecule, is membrane impermeant, and hence it acts to stain the nuclei of cells with injured (permeable) membranes (29; 44). Since ethidium bromide labels cells with a range of injury from minor (increased permeability) to cellular death, this technique cannot distinguish injury from lethality. Fluorescent illumination with the appropriate filters for EB (Ex=482 nm; Em=610 nm) and BB (Ex=343 nm and Em=483 nm) were applied. Tissue injury was examined in 5 fields of view for each group (control and CS) of EICP. Cellular injury was expressed as the ratio of ethidium bromide-labelled nuclei to bisbenzimide-labelled nuclei (EB/BB) (29; 44).

Analysis of Leukocytes

Leukocyte rolling and adherence were observed in post-capillary venules using the 40× objective (final magnification, 1400×) post fasciotomy. The total number of rolling and adherent leukocytes were measured over 30 seconds and expressed as the number per 1000 µm2. An adherent leukocyte was defined as a cell that remained stationary for a minimum of 30 seconds. Measurements of rolling and adhered leukocytes from each of the 5 fields of view were observed in both the control and experimental group.

Statistical Analysis

Statistical analysis consisted of a repeated measures two-way analysis of variance testing (ANOVA) to compare the degree of perfusion, muscle injury, leukocyte rolling and leukocyte adherence with the presence of compartment syndrome. Statistical significance was defined as $p<0.05$.

Results

Microvascular Dysfunction

The effects of increased duration of elevated intracompartmental pressure on capillary flow are shown (FIG. 1). The capillary profile observed in control animals demonstrates predominately continuous perfusion, representing normal healthy perfusion.

The number of continuously perfused capillaries (mean±SEM) decreased from 78.4±3.2/mm in the control group to 41.4±6.9/mm at 45-minute compartment syndrome ($p<0.05$). Perfusion shifted from a predominantly continuous profile in the control animals, to an intermittent and non-perfused profile in the compartment syndrome group. There was an increase in the number of intermittently perfused capillaries from 10.4±2.7/mm to 31.4±6.0/mm in the experimental group (p<0.05). The number of non-perfused capillaries increased from 12.7±1.4/mm in the control group, to 30.0±6.7/mm following 45 min of EICP (CS group) (p<0.05).

Inflammation

Figure 2:
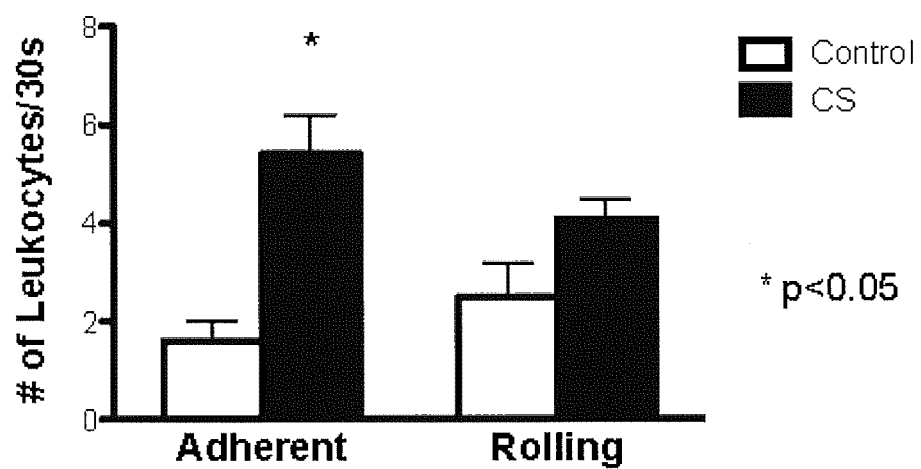
FIG. 2 is a graph illustrating leukocyte rolling and adherence in post-capillary venules observed in control and at 45 min of elevated intra-compartmental pressure.

Leukocyte number and flow characteristics increased in response to compartment syndrome. The mean number of activated leukocytes increased from 3.6±0.7/30 s in the control group to 8.6±1.8/30 s in the 45-minute compartment syndrome. Rolling leukocytes observed increased from 2.5±0.7/30 s in the control animals to 4.1±0.4/30 s in the experimental group. Adherent leukocytes significantly increased from 1.6±0.4/30 s in control group to to 5.4±0.8/30 s in experimental animals (p<0.005) (FIG. 2).

Tissue Injury

Figure 3:
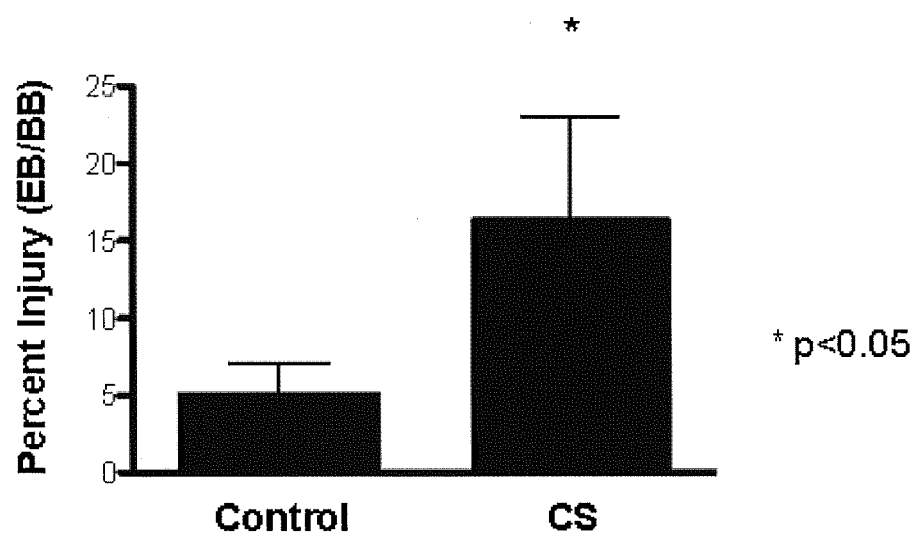
FIG. 3 is a graph showing effect of elevated intra-compartmental pressure on parenchymal tissue injury within the EDL muscle.

Muscle injury was quantified as the ratio of EB/BB stained nuclei and represents the percent injured cells per field (FIG. 3). After application of the fluorescent dyes, the control group demonstrated a baseline level of tissue injury (5.0±2.1%), presumed to be secondary to tissue handling during surgical preparation. There was a sudden and significant (p<0.05) increase in the percentage of injured cells (16.3±6.8%) in the CS group.

Model Characteristics

Figure 4:
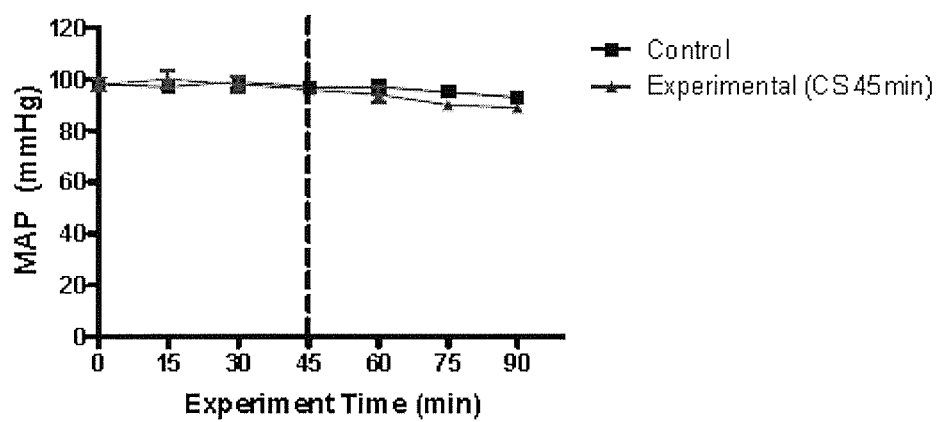
FIG. 4 is a graph showing Mean arterial pressure of rats. Mean arterial pressure measurements of control and compartment syndrome animals. The values were not significantly different and remained within physiologic limits.

Carotid artery cannulation demonstrated a normotensive model throughout the duration of CS. Mean arterial pressure was maintained within physiologic limits (FIG. 4).

Discussion

The effect of elevated intracompartmental pressure on microvascular perfusion, tissue injury and inflammation was studied in a small animal model of compartment syndrome using intravital video microscopy and nuclear fluorescent dyes. Direct imaging of capillaries demonstrated a significant decrease in continuously perfused capillaries (p<0.05) with a significant increase in intermittent and non-perfused capillaries (p<0.05)(FIG. 1). This observation characterizes the early microvascular response to the compartment syndrome insult. Continuous perfusion is normal physiologic perfusion observed in uninjured microvasculature. The immediate response to CS is a shift to intermittent and non-perfused capillaries. This state of diminished microvascular flow produces a non-nutritive perfusion with compromised gas exchange. Intermittent perfusion demonstrates a marked decrease in red cell flow whereas in non-perfused capillaries red cells have no movement. Post-fasciotomy intermittently perfused capillaries may recover flow; however, non-perfused capillaries do not (45).

This microvascular dysfunction is accompanied by a substantial inflammatory response (FIG. 2). Activated leukocytes are categorized as rolling or adherent, and were measured in the post-capillary venule. Leukocyte adherence was significantly increased (p<0.05) in CS animals as compared to controls. There was no observed difference in leukocyte rolling between groups. At 45 minutes the observed leukocyte adherence reflects a relatively early time course for leukocyte accumulation (32). Leukocyte arrest during rolling is triggered by chemoattractants and is mediated by the interaction of integrins to immunoglobulins expressed by endothelial cells (46). The arrest of leukocytes under conditions of flow and the leukocyte recruitment and emigration observed suggests that compartment syndrome induces a pro-inflammatory environment. The inflammatory activity seen in this model of compartment syndrome exceeds the degree of inflammation noted in complete ischemia and early reperfusion models (32). The exact role of inflammation in muscle damage in compartment syndrome is unknown, but may contribute to the non-reflow of capillaries as well as cellular injury.

Parenchymal injury was evidenced by the sudden significant increase in number of EB-labelled nuclei in the CS group as compared to control animals (p<0.05) (FIG. 3). Ethidium bromide is a fluorescent dye, which does not penetrate the cell membrane of uninjured cells (44). Injured cells develop increased membrane permeability and allow EB to enter the cell and stain the nucleus, thereby reflecting the amount of injury within the capillary networks observed. Whether these cells are able to recover or become functionally viable remains unknown. This technique for detecting injury has been used in vivo for many years in studying microcirculation and ischemia reperfusion (42; 29; 44).

CS as Low-Flow Ischemia

After 45 minutes of compartment syndrome nearly all of the capillaries observed in the EDL muscle displayed altered perfusion. Despite microvascular dysfunction in acute CS, some degree of perfusion remains at all times, creating a partial ischemic environment, or "low-flow" ischemia within the limb. This allows neutrophils to be activated immediately, which may contribute to the degree of cellular injury noted (31).

Following complete ischemia, revascularization leading to the reintroduction of oxygen into ischemic tissue results in an increase in reactive oxygen metabolites, initiating an acute state of inflammation (30). These reactive metabolites serve as a trigger to increase the overall rate of cellular apoptosis and necrosis (47). During EICP (30 mmHg) in a normotensive model with partially sustained perfusion, a concurrent amplification of the inflammatory system from reactive metabolites may occur since oxygenated blood continues to perfuse the compartment, in contrast to complete ischemia. In a murine model comparing complete hindlimb ischemia to partial ischemia, Conrad et at (51) reported that partial ischemia causes a significant early increase in the pro-inflammatory cytokine KC which is analogous to human IL-8 expressing neutrophil chemotactic activity. This finding corroborates the early inflammatory response we observed in compartment syndrome, which we believe is physiologically similar to a partial ischemic state. In a canine model comparing complete ischemia to compartment syndrome, Heppenstall et al (48) observed that the compartment syndrome stimulus causes severe acidosis and metabolic stress. He also concluded that compartment syndrome renders a more severe degree of muscle ultrastructural deterioration than ischemia alone. CS was found to be more injurious to muscle than complete ischemia, possibly due to the cytotoxic inflammation induced by this low flow ischemic state. Our physiologic model of CS includes a "low-flow" ischemic state with associated inflammatory activation and muscle tissue injury.

Compartment Syndrome Modelling

The severity and acuity of compartment syndrome restricts the study of its pathophysiology in humans. Animal models have been applied in the study of compartment syndrome since 1926 when Jepson published an inaugural study in canines. He experimentally induced compartment syndrome and detailed the functional benefit of decreasing "venous obstruction" via fasciotomy. Animal models of acute lower-extremity compartment syndrome have been developed using various techniques in both large and small animals. Skin fold chambers, arterial occlusion via Fogerty balloon, arterial ligation, inflation of latex balloons within compartments, external compression and tourniquet application are some of the techniques published (8; 49). Large animal canine models deemed clinically relevant have induced compartment syndrome using pressure-controlled autologous blood or plasma infusion into compartments.

In the present study, a model with pressure-controlled isotonic normal saline infusion in a rodent hindlimb was utilized. We studied the EDL muscle, as it is composed of a mixture of muscle fiber types, with up to 54% of the muscle being fast twitch (43), similar to human anterior compartment musculature. The EDL preparation has been established in the study of microcirculation (29; 43; 32; 44), its advantages being that it is a deep muscle and sustains minimal mechanical manipulation in its preparation and therefore minimal reactive hyperemia and injury. The majority of the muscle remains in situ when its microcirculation is studied, its surgical preparation does not demonstrate deterioration of perfusion with time and hence experimental controls can be easily applied.

The time chosen for elevation of compartment pressure (45 min) was based on previous work demonstrating that 1 hour of ischemia in a rodent approximates 4 hours of ischemia in a human (50). The experimental time of 45 minutes was applied in order to observe the early microvascular response to EICP and its subsequent effects on the surrounding tissue. Small animal models are not identical to metabolic and cellular derangements in humans and hence experimental effects need to be compared to the existing body of literature. This model is reliable and simple to use for the study of microcirculation, inflammation and injury in acute compartment syndrome and allows for detailed study of the mechanism underlying compartment syndrome.

To our knowledge, this study provides the first evidence of the in vivo microvascular perfusion changes that occur with early compartment syndrome. The use of intravital microscopy in conjunction with fluorescent stains in a small animal model has demonstrated the specific perfusion changes, inflammation and tissue injury that occur in early CS. This data suggests that the injury process in CS begins early and causes a severe inflammatory response.

Example 2

Inflammatory Contribution to Cellular Injury in Compartment Syndrome

Introduction

Compartment syndrome (CS) is a devastating complication of musculoskeletal trauma, caused by increased pressure within a closed osseofascial compartment (1-5). A large body of literature has determined that the inaugural pathophysiological event in the development of CS is a result of increased intracompartmental pressure, leading to microcirculatory dysfunction. This, in turn, limits oxygen and nutrient delivery, giving rise to cellular anoxia and tissue necrosis (1, 3, 5, 8). The final common pathway is severe myonecrosis, which often results in permanent functional impairment or even loss of the limb. Unlike complete ischemia, however, CS causes tissue necrosis in the face of patent vessels; paradoxically, ischemia ensues with a distal pulse present (41), indicating the pathophysiology is more complex than previously understood.

Direct live in vivo imaging of the capillaries in CS has demonstrated significant microvascular impairment coupled with a substantial increase in activated leukocytes in skeletal muscle postcapillary venule (9). The observed low-flow ischemic state maintains a diminished level of microvascular blood flow associated with a rapid activation of leukocytes, suggesting that early cellular injury in CS may result from a combination of ischemia and acute inflammatory damage.

Intravital video microscopy (IWM) studies in animal models of complete hindlimb ischemia and reperfusion (I/R) have demonstrated that activated leukocytes adhering to postcapillary venules directly impair capillary perfusion (32), while increasing vascular protein leakage and edema (31). Leukocytes also cause direct parenchymal injury following reperfusion (29, 32).

The pathologic contribution of inflammation to the pathophysiology of CS is being increasingly recognized; studies from our group (9) and others (10) have broadly implicated leukocytes as playing a role in both microvascular and parenchymal injury during CS.

Inflammation, being subject to modulation, may therefore provide an opportunity to attenuate injury in the muscle subjected to elevated intra-compartmental pressure (ICP).

In this study, normal rodents exposed to elevated ICP were compared with leukopenic rodents, to determine the direct contribution of inflammation to the cellular injury in CS using both IVVM and histochemical staining techniques. It was hypothesized that leukopenia would provide significant microvascular and parenchymal protection compared to rodents with intact immunity. These results may thus provide evidence toward a potential therapeutic benefit for anti-inflammatory treatment of elevated ICP.

Methods

Animal Handling and Care

Male Wistar rats (175-250 g) utilized for these experiments had access to food and water ad libitum. Animal housing, care and associated protocols were conducted in agreement with the Canadian Council on Animal Care. The animal protocol was this study was approved by the Animal Use Subcommittee at the University of Western Ontario.

Experimental Protocol

Fifty rats were randomly assigned into two groups: control (n=25) and leukopenia (n=25). Rats were rendered leukopenic by a single injection of high dose cyclophosphamide (250 mg/kg IP, Procytox™, Deerfield Ill.) three days prior to induction of CS. Complete blood count (CBC) was ordered for each animal to ensure leukopenia at 72 hours post-injection; samples were processed at the clinical biochemistry laboratory at the London Health Sciences Centre (London, Ontario, Canada). The animals were anaesthetized with isoflurane (5% induction, 2% maintenance) in a 1:1 $O_2$:$N_2$ mixture for the whole duration of the experiment. The left carotid artery was cannulated to monitor mean arterial pressure.

Compartment Syndrome

Compartment pressure was elevated by an infusion of isotonic normal saline via a 24-gauge angiocatheter into the anterior compartment of the left hind limb, as described previously (9). The ICP was measured by an electronic compartmental pressure monitoring system (Synthes USA, Paoli, Pa.), inserted through 14-gauge angiocatheter. Sham animals (n=10) underwent all procedures as CS groups, but the ICP was kept at the baseline of 0 mm Hg. In CS animals, the ICP was maintained between 30-40 mmHg for 45- (n=10), 90- (n=10), 120- (n=10) and 180-minute (n=10) time intervals. These were then followed by fasciotomy and intravital video microscopy (IVVM), in order to assess the degree of microvascular dysfunction, leukocyte activation and irreversible injury to muscle cells.

Intravital Video Microscopy (IVVM)

Following fasciotomy, the extensor digitorum longus (EDL) muscle was prepared for IVVM, as previously described (9, 29). Briefly, the EDL was dissected to the level of its distal tendon, which was then tied with a suture and cut from its bony insertion. The animal was transferred onto the stage of an inverted microscope (Nikon); the EDL was reflected into a saline bath containing 5 mg/ml each of the fluorescent vital dyes bisbenzimide (BB; exc. 343 nm, em. 483 nm) and ethidium bromide (EB; exc. 482 nm, em. 616 nm). BB stains the nuclei of all cells while EB stains the nuclei of only those cells with damaged cell membrane; thus, EB/BB ratio provided an index of tissue injury.

Microvascular perfusion and leukocytes within the post-capillary venules were recorded by transillumination with 20× and 40× objectives, respectively, in five adjacent fields of view. Fluorescence microscopy was used to visualize the BB and EB from the same fields of view that had been selected for the measurement of capillary perfusion. At the conclusion of the experiment, rats were euthanized by an overdose of anesthetic agent.

Offline Video Analysis

Capillary perfusion was assessed by counting the number of continuously perfused (CPC), intermittently-perfused (IPC) and non-perfused (NPC) capillaries that crossed three parallel lines drawn perpendicular to the capillary axis on the video monitor, and was expressed as % of total capillaries. Tissue injury was assessed by counting the number of EB- and BB-labelled nuclei, and expressed as EB/BB ratio. Leukocyte activation was assessed by counting the numbers of rolling and adherent leukocytes in post-capillary venules and expressed per unit area (i.e. 1000 mm2). Venular area was measured using ImageJ (NIH, Bethesda, Md.). A leukocyte was considered adherent if it remained stationary for at least 30 seconds, and a cell was considered rolling if it remained in contact with the wall of the vessel during its movement.

Statistical Analysis

Statistical analysis consisted of a repeated measures two-way analysis of variance (ANOVA) to compare the degree of perfusion, muscle injury, leukocyte rolling and leukocyte adherence in the presence of compartment syndrome, in both the control and leukopenic animals at 45, 90, 120 and 180 minutes of elevated ICP. Statistical significance was defined as $p<0.05$.

Results

Microvascular Perfusion

Figure 5:
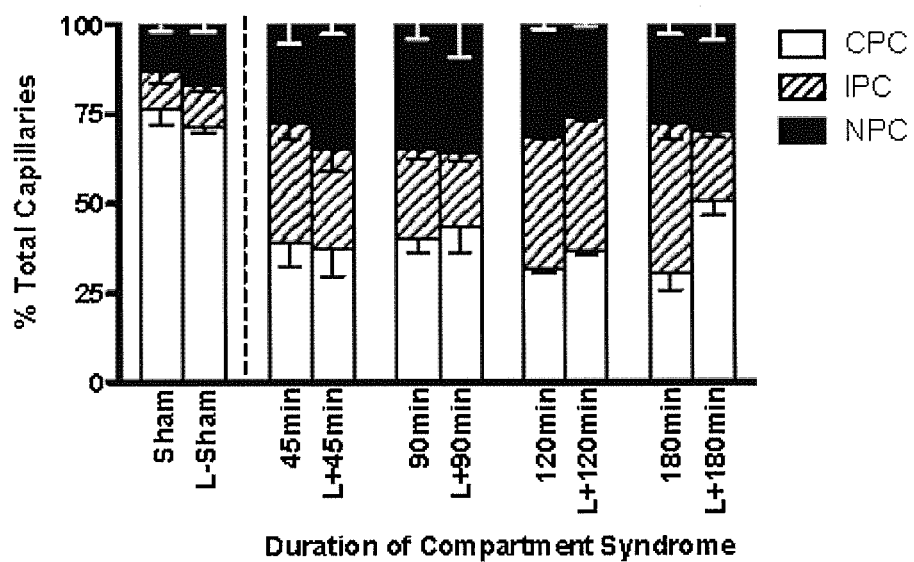
FIG. 5 is a graph illustrating the effect of leukopenia on microvascular perfusion following compartment syndrome (CS), measured using intravital video microscopy. L, leukopenic animals; CPS, continuously-perfused capillaries; IPC, intermittently-perfused capillaries; NPC, nor-perfused capillaries.

The effect of elevated ICP on microvascular perfusion is shown in FIG. 5. Both control and leukopenic groups demonstrated an observed reduction in capillary perfusion at all experimental time points. The capillary profile observed in sham animals demonstrates predominately continuous perfusion, representing the expected normal healthy perfusion. In the control CS group, the number of CPC (mean±SEM) decreased from 76.5±5.1% in sham to 38.8±7.1%, 36.4±5.7%, 32.0±1.7%, and 30.5±5.35 at 45, 90, 120 and 180 min CS animals, respectively ($p<0.05$). In the leukopenic group, the perfusion profiles demonstrated a similar trend in microvascular dysfunction: CPC decreased from 71.5±2.1% in sham to 39.2±8.6%, 43.5±8.5%, 36.6±1.4% and 50.8±4.8% at 45, 90, 120 and 180 min CS, respectively ($p<0.05$). Thus, the perfusion shifted from a predominantly continuous profile in the sham to an intermittent and non-perfused profile in the CS animals, in both the control and leukopenic groups. No statistical significance was demonstrated between the experimental (i.e. leukopenic) and control groups.

Tissue Injury

Figure 6:
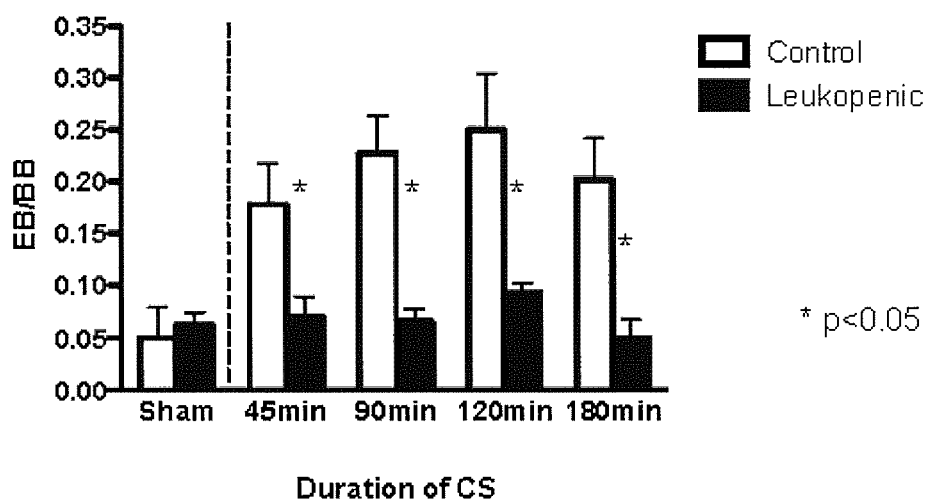
FIG. 6 is a graph showing the effect of leukopenia on parenchymal tissue injury within the EDL muscle following CS ($p<0.05$).

Muscle injury was quantified as the ratio of EB/BB stained nuclei, and is represented as the percent of injured cells per field of view (FIG. 6). Muscle injury was significantly increased in the control group (i.e. normal leukocyte count) from 5.0±3.0% in sham animals to 18.0±4.0% at 45 minutes, 23.0±4.0% at 90 minutes, 32.0±7.0% at 120 minutes, and 20.0±5.0% after 180 minutes of elevated ICP. Leukopenia itself had no effect on muscle injury, as seen in the leukopenic sham animals. When leukopenic animals were subjected to elevated ICP, there was a significant decrease in tissue injury observed at all time intervals: 7.0±2.0% at 45 minutes, 7.0±1.0% at 90 minutes, 9.0±1.0% at 120 minutes, and 5.0±2.0% at 180 minutes of elevated ICP; this level of injury was significantly lower in the leukopenic group, as compared to control animals (FIG. 6)

Inflammation

Figure 7:
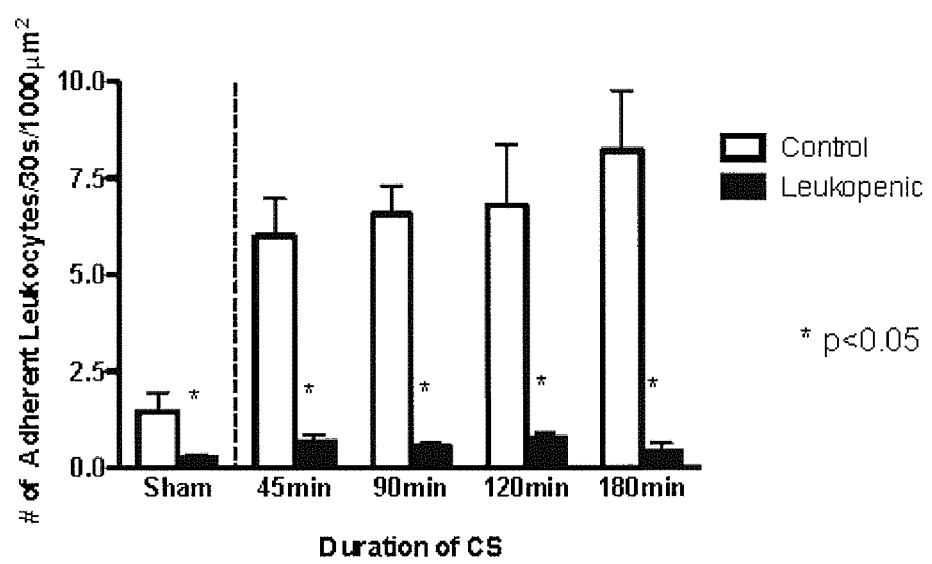
FIG. 7 is a graph illustrating the effect of leukopenia on leukocyte activation (adherent leukocytes) following CS. Leukopenic animals showed a significant decrease (*$p<0.05$).

Leukocyte activation and flow characteristics were significantly upregulated by the CS insult (FIG. 7). Leukocyte adhesion to the vascular endothelium increased from 1.5±0.55 leukocytes/30 s/1000 mm2 in sham animals to 6.0±1.06, 6.6±0.77, 6.8±1.84 and 8.2±1.81 leukocytes/30 s/1000 mm2 at 45, 90, 120 and 180 min CS, respectively ($p<0.05$). Leukopenia significantly blocked leukocyte activation at all experimental time points: adhesion was diminished in sham rodents to 0.3±0.11 leukocytes/30 s/1000 mm2, and continued to remain blunted to 0.7±0.18, 0.6±0.11, 0.8±0.15, and 0.4±0.27 leukocytes/30 s/1000 mm$^2$ at 45, 90, 120 and 180 min CS, respectively ($p<0.05$) (FIG. 7).

Figure 8:
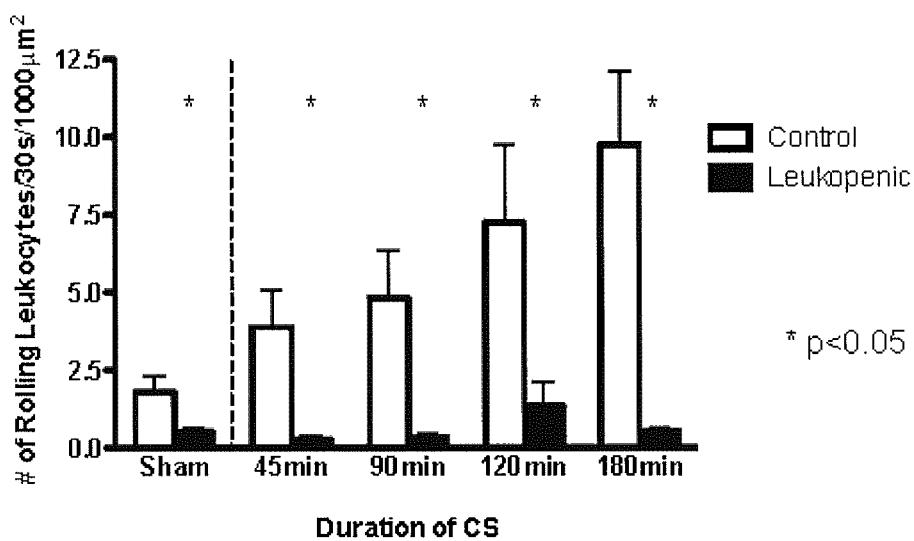
FIG. 8 is a graph illustrating the effect of leukopenia on leukocyte activation (rolling leukocytes) following CS. Leukopenic animals showed a significant decrease (*$p<0.05$).

A similar trend was demonstrated in rolling leukocytes, with a significant increase at all experimental time points as compared to sham in normal rodents. Rolling behaviour increased from 1.8±0.59 leukocytes/30 s/1000 mm2 to 3.9±1.6, 4.8±1.65, 7.3±2.90 and 9.8±2.73 leukocytes/30 s/1000 mm2 at 45, 90, 120 and 180 min CS, respectively (FIG. 8). Leukopenic animals did not mount a significant inflammatory response; leukocyte rolling did not increase between sham and 45 min of elevated ICP, and remained at 0.5±0.19 leukocytes/30 s/1000 mm2. Rolling also remained low at 0.3±0.10 leukocytes/30 s/1000 mm$^2$ at 90 min CS, with just a slight, non-significant increase to 2.7±1.34 leukocytes/30 s/1000 mm$^2$ at 120 min CS. Finally, at 180 min CS, the rolling returned back to sham levels, at 0.6±0.07 leukocytes/30 s/1000 mm$^2$ (FIG. 8).

Discussion

The pathophysiological mechanisms that underlie the severe and acute myonecrosis observed in CS are complex and not fully understood. This study was designed to examine the relative contribution of inflammation to tissue injury in a model of CS. By rendering the animals leukocyte deplete, a very rigid control was applied in order to accurately quantify the relative contribution of inflammation to parenchymal injury in animals subjected to elevated ICP over time. We studied the effect of elevated ICP in a leukocyte deplete rodent model, assessing microvascular perfusion, inflammation and tissue injury, utilizing IVVM and fluorescent dye staining.

Tissue Perfusion

Perfusion under normal, non-traumatic conditions exhibits continuous physiologic flow, with a constant stream of red blood cells travelling though capillaries. The CS insult demonstrated a significant shift from continuous perfusion in sham animals to increased intermittent and non-perfused capillaries across all time points. Interruption of flow rate and volume leads to intermittent perfusion which, in turn, compromises gas exchange. Non-perfused capillaries exist when complete arrest of red cell are observed in the capillary bed, leading to no nutrient or gas exchange: essentially, a state of ischemia (9). This shift in flow demonstrates a pathologic microvascular perfusion in response to the CS insult, shown in vivo, under live conditions. The microvascular dysfunction occurred early, and appeared to persist over time. With increased proportion of non-perfused capillaries in the presence of continuous perfusion within the same capillary bed, a low flow ischemic state is established in CS. The effect of no-flow ischemia on skeletal muscle has been well studied in the literature (39). As the duration of ischemia increases, predictable changes in the microcirculation such as increased vascular permeability to plasma proteins and progressive interstitial edema ensue (31). In CS, leukocyte deplete animals demonstrated no significant difference (p<0.05) in the blood flow rate or flow characteristics at 45, 90, 120 an 180 minutes of CS, as compared to controls (FIG. 5).

Microvascular perfusion was essentially unchanged in leukopenic animals, as compared to controls; hence leukopenia was not protective in restoring or maintaining perfusion in the face of elevated compartment pressure. This data suggests that the effects of leukocytes on the microvascular perfusion in CS are, perhaps, pathophysiologically different from a pure ischemia-reperfusion insult with respect to skeletal muscle microcirculation. In a leukocyte deplete ischemia reperfusion model, microvascular dysfunction (i.e. no reflow phenomenon) was prevented, and parenchymal injury diminished in the presence of leucopenia (32). In our studies, however, while perfusion was altered in CS, leukopenia did not have a direct effect on the magnitude of microvascular dysfunction, suggesting that although ischemia-reperfusion pathophysiology may share features with CS, there may be a distinct pathophysiology causing microvascular dysfunction.

Inflammation

The results of our study demonstrate that the CS insult is accompanied by a substantial inflammatory response. At 45 minutes of CS, we observed the arrest of leukocytes under conditions of flow, recruitment of activated leukocytes and extravasation, which strongly suggests that CS induces a pro-inflammatory environment. Leukopenia significantly diminished leukocyte activation, both in terms of rolling and firm adhesion in the post-capillary venules at 45, 90, 120 and 180 minutes of CS as compared to controls (p<0.05) (FIG. 6). Leukocyte-endothelial interactions in the conditions of trauma, injury, infection and ischemia are known to create a pro-inflammatory environment secondary to the upregulation of cytokines and chemokines, which stimulate leukocyte activation and recruitment of polymorphonuclear leukocytes (PMNs) into the area of injury (ref). Activated leukocytes produce reactive oxygen species and proteolytic enzymes, causing cellular damage, increasing permeability and edema, resulting in increased interstitial pressure; this may lead to non-perfused segments in the microvascular beds (30, 32, 40).

Tissue Injury

Parenchymal injury was evidenced by the significant increase in the number of EB-labelled nuclei in the CS group, as compared to control animals (p<0.05). All experimental groups demonstrated a more than 50% significant reduction in tissue injury as compared to controls (FIGS. 7 and 8). This data suggests that inflammation is a significant pathophysiologic mechanism driving injury in experimental CS. Leukocyte adhesion and interaction with the endothelium appears to be important to the development of tissue injury without significant effect on capillary perfusion. This would suggest that in early CS, inflammation may be more important and perhaps with prolonged exposure to CS late ischemia may be more pathophysiologically relevant.

This study demonstrates that inflammation should be considered central to the understanding of the pathogenesis of cellular injury in CS. Perhaps, modulation of inflammation may diminish myonecrosis in CS. The specific inflammatory pathways or signaling systems still need to be clearly delineated, as well as whether the leukocyte activation and adhesion remain temporally uncoupled from the observed microvascular dysfunction.

Example 3

The Severity of Microvascular Dysfunction Due to Compartment Syndrome is Diminished by the Systemic Application of CO-Releasing Molecules (CORM-3)

Materials and Methods

Animal Preparation

The experimental protocol was approved by the Council on Animal Care of the University of Western Ontario, and has been previously described in detail [9]. Briefly, male Wistar rats (body weight 180-250 g) were anesthetized by inhalational isoflurane (5% induction, 2% maintenance) in 1:1 oxygen/nitrogen mixture. Left carotid artery was cannulated to allow for the monitoring of systemic blood pressure, fluid administration and blood sampling.

Compartment pressure monitoring probe (Synthes, Westchester Pa.) was inserted into the posterior compartment via gauge 16 angiocatheter (BD), while gauge 24 angiocatheter (BD) attached to an IV line was placed into the anterior compartment of the rat hind limb. CS was induced by an infusion of isotonic saline, leading to an elevation of intra-compartmental pressure (ICP) to 30 mmHg. Elevated ICP was maintained for 2 hours. Fasciotomy was performed to decompress the hind limb compartments; the muscles were allowed to reperfuse for 45 minutes, followed by intravital video microscopy.

CORM-3 Synthesis

A water-soluble CORM-3 (tricarbonylchloro-glycinate-ruthenium(II), [Ru(CO)3Cl-glycinate]; molecular weight 295 gmol-1) was synthesized in collaboration with Dr. F. Capretta (McMaster University, Hamilton, Ontario, Canada) in accordance with the previously-published method. [17] CORM-3 (10 mg/ml stock solution) was prepared fresh by dissolving it in isotonic saline just prior to injection. As a control, inactive CORM-3 (iCORM-3) was generated by dissolving CORM-3 in saline 72 hours prior to the experiment and allowing it to release all CO from the solution.

Experimental Groups

Rats were randomly assigned to one of four experimental groups: sham (n=4), CS (n=4), CS+CORM-3 (n=8) and CS+iCORM-3 (n=8). CO-releasing molecule-3 (CORM-3), or its inactive form (iCORM-3), was administered to animals undergoing CS upon fasciotomy at the dose of 10 mg/kg, IP. Sham animals underwent all the procedures as CS groups, but they did not receive saline infusion into the anterior compartment of the hind limb, and the ICP was maintained at the baseline level (0 mmHg).

Intravital Video Microscopy (IVVM)

The extensor digitorum longus (EDL) muscle was dissected to the level of its distal tendon, which was tied with a suture and cut from its bony insertion. The animal was transferred onto the stage of an inverted microscope (Nikon™); the EDL was reflected into a saline bath containing 5 µg/ml each of the fluorescent vital dyes bisbenzimide (BB; exc. 343 nm, em. 483 nm) and ethidium bromide (EB; exc. 482 nm, em. 616 nm). BB stains the nuclei of all cells while EB stains the nuclei of only those cells with damaged cell membrane. Thus, EB/BB ratio provided an index of tissue injury.

Microvascular perfusion and leukocytes within the post-capillary venules were recorded by translumination with 20× and 40× objectives, respectively, in five adjacent fields of view. Fluorescence microscopy was used to visualize the BB and EB from the same fields of view that had been selected for the measurement of capillary perfusion. At the conclusion of the experiment, rats were euthanized by an overdose of anesthetic agent.

Offline Video Analysis

Capillary perfusion was assessed by counting the number of continuously-perfused (CPC), intermittently-perfused (IPC) and non-perfused (NPC) capillaries that crossed three parallel lines drawn perpendicular to the capillary axis on the video monitor, and was expressed as % of total capillaries. Tissue injury was assessed by counting the number of EB- and BB-labelled nuclei, and expressed as EB/BB ratio. Leukocyte activation was assessed by counting the numbers of rolling and adherent leukocytes in post-capillary venules and expressed per 1000 $\mu m^2$. Venular area was measured using ImageJ (NIH, Bethesda, Md.). A leukocyte was considered adherent if it remained stationary for at least 30 seconds, and a cell was considered rolling if it remained in contact with the wall of the vessel during its movement.

Serum Tumour Necrosis Factor Alpha (TNF-α) Measurements

TNF-α levels were measured from arterial blood samples drawn at 9 time points: (1) baseline, (2) 15 minutes into CS, (3) 45 minutes into CS, (4) 90 minutes into CS, (5) 2 hours into CS-just prior to fasciotomy and CORM-3 (or iCORM-3) injection, (6) 10 minutes post-fasciotomy, (7) 20 minutes post fasciotomy, (8) 30 minutes post fasciotomy, (9) 45 minutes post fasciotomy, just before IVVM. TNF-α was assessed using enzyme-linked immunosorbent assay (ELISA, Pierce Biotechnology, c/o Thermo Scientific, Rockford, Ill.) according to manufacturer's instructions. The TNF-α ELISA was sensitive to less than 5 μg/mL.

Statistical Analysis

All parameters were expressed as mean±SEM and analyzed using one-way ANOVA. $p<0.05$ was considered statistically significant.

Results

Systemic Leukocyte Counts and Carboxyhemoglobin (COHb)

Elevation of ICP, coupled with subsequent fasciotomy and 45 minutes of reperfusion, led to a small, but significant rise in leukocyte counts; CORM-3 treatment was able to decrease the severity of this response (see Table 1). Application of CORM-3 or iCORM-3 had no effect on COHb levels (see Table 1).

TABLE 1

The effects of CORM-3 on systemic leukocytes and COHb

| | LKC (Units × $10^9$/L) | Hemoglobin (g/L) | COHb (%) |
| --- | --- | --- | --- |
| Sham | 1.5 ± 0.2 | 125.0 ± 2.3 | 1.5 ± 0.2 |
| CS | 3.9 ± 0.8 | 125.3 ± 3.3 | 1.5 ± 0.1 |
| CS + iCORM-3 | 4.1 ± 0.7* | 124.8 ± 2.9 | 1.6 ± 0.1 |
| CS + CORM-3 | 2.3 ± 0.2† | 129.5 ± 2.7 | 1.6 ± 0.1 |

Two hours of elevated ICP were followed by fasciotomy, injection of CORM-3 (or iCORM-3) and 45 min reperfusion. CS-associated rise in systemic leukocytes was reversed by CORM-3 application (*$p<0.01$ from sham; †$p<0.05$ from CS+iCORM-3). CORM-3 and iCORM-3 caused no changes in systemic levels of COHb. LKC, leukocyte counts; COHb, carboxyhemoglobin.

Microvascular Perfusion

Figure 9:
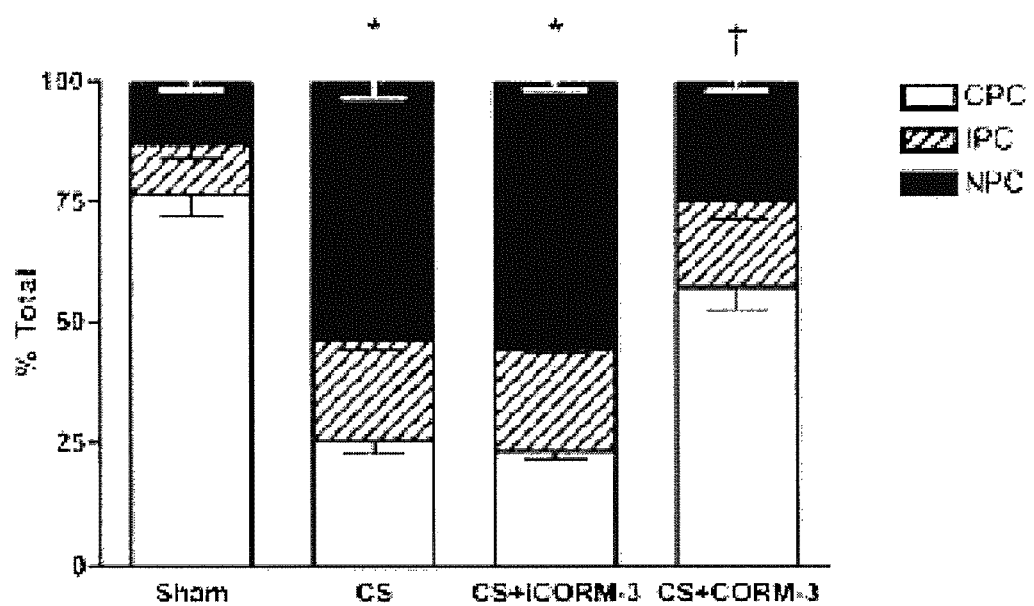
FIG. 9 is a graph showing the effect of CORM-3 on skeletal muscle microvascular perfusion following CS. Two hours of elevated ICP were followed by fasciotomy, injection of CORM-3 (or its inactive form, iCORM-3), 45 min reperfusion and IVVM. CS-associated perfusion changes were reversed by CORM-3 application (*$p<0.001$ from sham; †$p<0.001$ from CS+iCORM-3). CPC, continuously-perfused capillaries; IPC, intermittently-perfused capillaries; NPC, non-perfused capillaries.

Elevation of ICP resulted in significant changes to microvascular perfusion, as shown in FIG. 9. The number of continuously-perfused capillaries (CPC) decreased from 76±4% in sham to 23±2% in CS+iCORM-3 (00.0001), while the number of non-perfused capillaries (NPC) increased from 13±2% in sham to 55±2% in CS+iCORM-3 ($p<0.0001$). CORM-3 treatment was able to restore the number of CPC to 57±5%, ($p<0.001$), while iCORM-3 had no effect.

Tissue Injury

Figure 10:
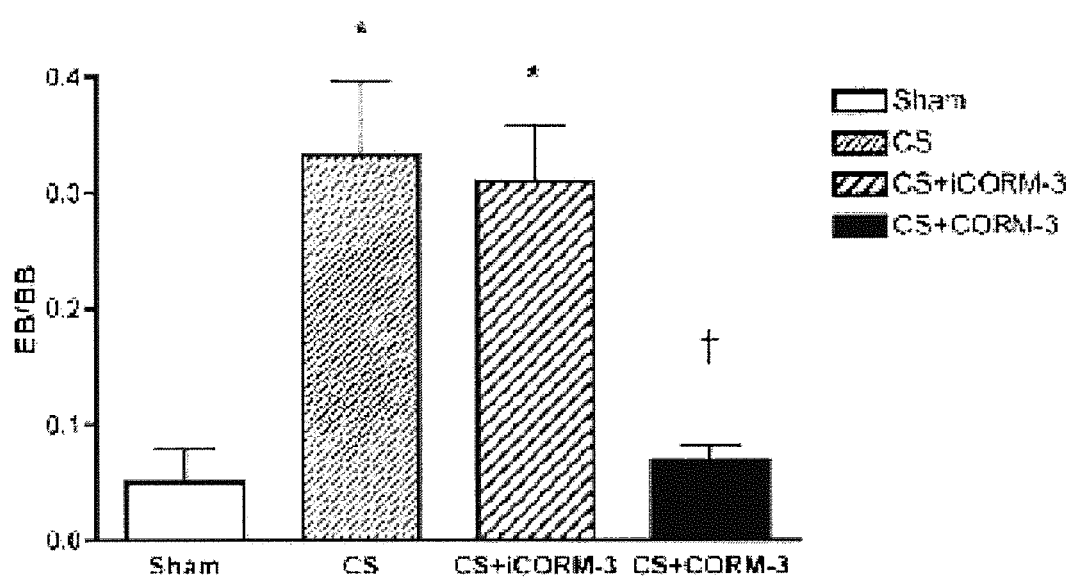
FIG. 10 is a graph showing the effect of CORM-3 on skeletal muscle tissue injury following CS. Two hours of elevated ICP were followed by fasciotomy, injection of CORM-3 (or its inactive form, iCORM-3), 45 min reperfusion, and IVVM. CS-associated tissue injury was reversed by CORM-3 application (*$p<0.001$ from sham; †$p<0.001$ from CS+iCORM-3).

Muscle injury, as measured by EB/BB ratio, significantly increased from 0.05±0.03 in sham to 0.31±0.05 ($p<0.0001$) in CS+iCORM-3 group. CORM-3 treatment was able to diminish tissue injury to 0.07±0.01 ($p<0.001$) (FIG. 10).

Serum TNF-α

Figure 11:
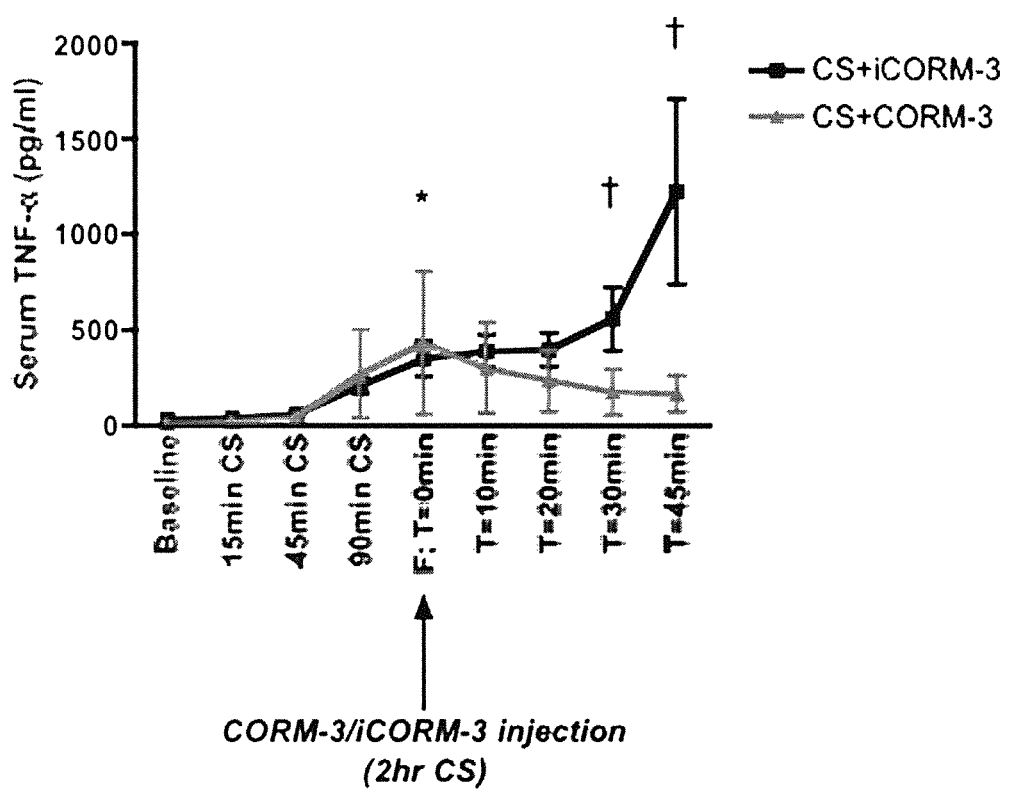
FIG. 11 is a graph showing the effect of CORM-3 on serum TNF-α expression in CS. Two hours of elevated ICP were followed by fasciotomy, injection of CORM-3 (or its inactive form, iCORM-3) and 45 min reperfusion. Serum TNF-α levels were assessed at each time point indicated. Any further post-fasciotomy TNF-α elevation was reversed by CORM-3 application (*$p<0.01$ from baseline; †$p<0.001$ from CS+iCORM-3). F, fasciotomy.

Elevation of ICP led to a progressive serum TNF-α release, reaching its maximum level at 2 hours (just prior to fasciotomy; $p<0.01$) (FIG. 11). TNF-α levels continued to rise in the post-fasciotomy/reperfusion period in animals treated with iCORM-3. In contrast, CORM-3 injection effectively prevented the latter response at 30 and 45 minutes post-fasciotomy ($p<0.001$) (FIG. 11).

Inflammation

Figure 12A:
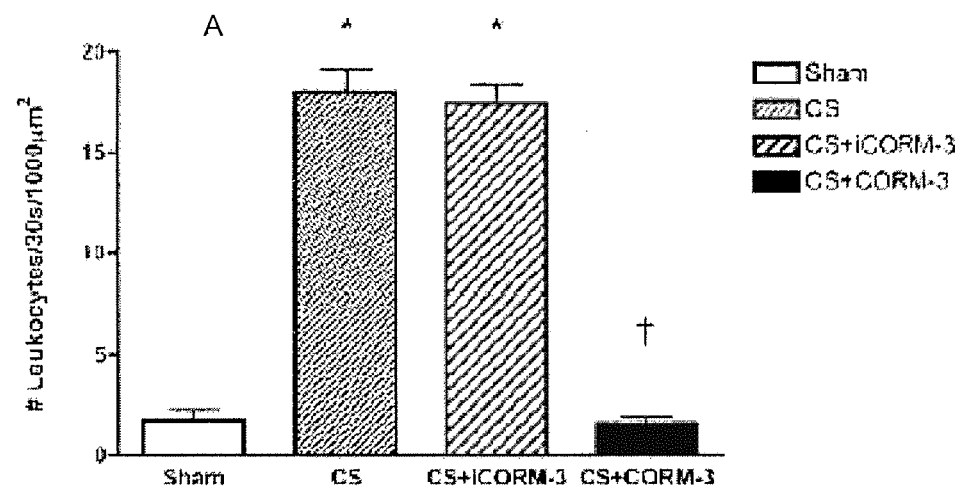
FIG. 12 are graphs showing the effect of CORM-3 on modulation of leukocyte recruitment to the skeletal muscle vasculature following CS. Panel A illustrates leukocyte adhesion and panel B illustrates leukocyte rolling. Two hours of elevated ICP were followed by fasciotomy, injection of CORM-3 (or its inactive form, iCORM-3), 45 min reperfusion and IVVM. CORM-3 application was able to prevent leukocyte adhesion within the post-capillary venules. (*$p<0.001$ from sham; †$p<0.001$ from CS+iCORM-3).
Figure 12B:
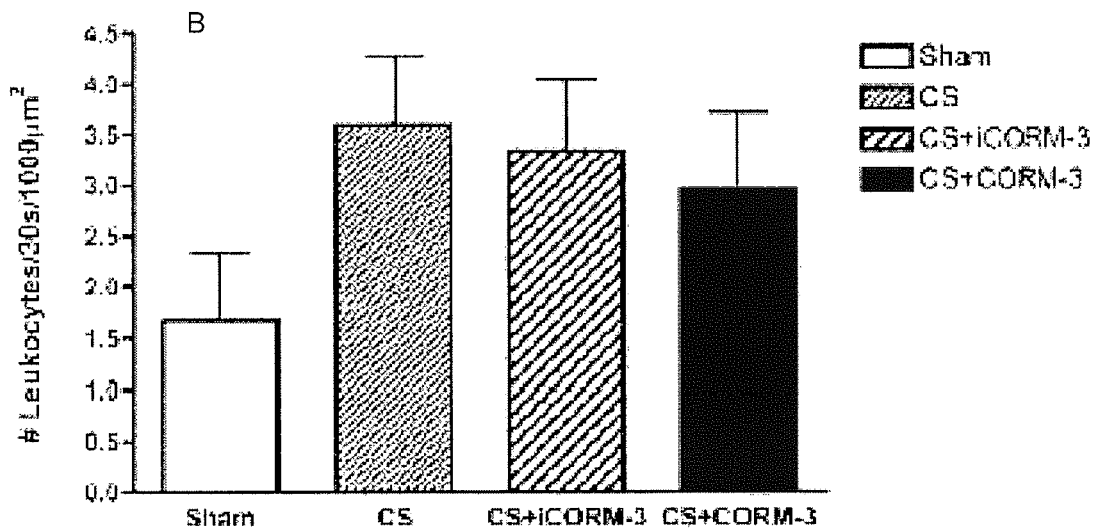

Elevation of ICP led to significant leukocyte activation, as demonstrated by the adhesive interactions with vascular endothelium. Leukocyte adherence in the post-capillary venules of the skeletal muscle was increased from 1.8±0.5 in sham to 13.7±0.9 leukocytes/30 s/1000 $\mu m^2$ in CS+iCORM-3 ($p<0.0001$) (see FIG. 12A). Leukocyte rolling, while not statistically significant, also increased from 1.7±0.6 to 3.3±0.7 leukocytes/30 s/1000 $\mu m^2$ (see FIG. 12B). CORM-3 treatment led to a significant, 8-fold decrease in leukocyte adherence, while having no effect on leukocyte rolling (0.6±0.3 adherent leukocytes/30 s/1000 $\mu m^2$, $p<0.001$ and 3.0±0.8 rolling leukocytes/30 s/1000 $\mu m^2$, not significant, respectively) (FIG. 12A and FIG. 12B).

Conclusion

The inventors investigated the effect of CO, liberated from a water-soluble CO donor (CORM-3), on the microvascular perfusion, inflammation and cellular injury of CS-challenged muscle. Direct visualization of the capillary bed through the use of IVVM demonstrated a significant decrease in the number of continuously-perfused capillaries and a significant increase in non-perfused capillaries in controls, i.e. animals treated with the inactivated CORM-3 (CS+iCORM-3) (FIG. 9). In addition to impaired capillary perfusion, the degree of parenchymal injury increased in the CS+iCORM-3 group compared to the sham group. Muscle injury, as evidenced by EB/BB-stained nuclei, was sudden and severe (FIG. 10).

Continuous perfusion is defined as a physiologic flow through the capillary bed, whereas intermittent perfusion results from a marked decrease in red blood cell flow. [9] Non-perfused capillaries are seen when no red cell movement is observed. The change from continuous perfusion to a predominantly non-perfused profile demonstrates a pathologic shift in the microvascular bed in response to CS. Animals treated with CORM-3 had shown significant improvement in capillary perfusion rates, restoring the number of continuously-perfused capillaries to levels comparable to those of the sham group (FIG. 9). Moreover, administration of CORM-3 essentially restored tissue injury levels back to baseline levels, as those seen in the sham group (FIG. 10).

CO is a signaling molecule made endogenously by the degradation of heme, catalyzed by heme oxygenase (HO). [28] CO can exert vasodilatory effects, mitigate intracellular apoptosis, suppress inflammatory pathways and have anti-ischemic effects. [18] In this Example 1, CORM-3 (a water-soluble formulation, administered IP) demonstrates a beneficial effect in preserving microvascular flow in CS-challenged muscle. Microvascular perfusion was virtually unchanged at 2 hours of elevated ICP in the presence of CORM-3, suggesting a substantial protective role of exogenously applied CO in the maintenance of skeletal muscle blood flow during CS. To the best of the inventors' knowledge, this is the first time that such potent protective effects of CORM-3 were demonstrated in an acute and overwhelming inflammatory onset, such as CS.

CS, a form of ischemia-reperfusion injury, produces a pro-inflammatory environment, resulting in the upregulation of cytokines and chemokines. [29] These, in turn, stimulate leukocyte activation (primarily polymorphonuclear leukocytes, PMN) and recruitment into the inflamed tissues. Once activated, leukocytes produce reactive oxygen species (ROS) and release proteolytic enzymes that (individually or concurrently) cause cellular damage and contribute to the increased vascular permeability, as well as subsequent formation of edema. As a result, increased interstitial pressure compresses adjacent capillaries, creating non-perfused segments. [30-32] In this Example 1, the inventors observed a marked increase in the levels of circulating TNF-$\alpha$ (one of the most potent pro-inflammatory cytokines) in CS-challenged animals, particularly post-fasciotomy. This was associated with overwhelming leukocyte recruitment to the CS-challenged muscle, as demonstrated by adherent leukocytes in the post-capillary venules (FIG. 12A). Interestingly, the increase in number of adherent leukocytes was completely prevented in animals treated with CORM-3, but not its inactive counterpart, iCORM-3. It is important to note that the decrease in leukocyte recruitment to CS-challenged muscle correlated with the CORM-3-dependent suppression of serum TNF-$\alpha$ levels (FIG. 11).

Using CS-challenged muscle in a rodent model, Example 1 demonstrates that the application of CORM-3 resulted in restoration of microvascular perfusion, 8-fold decrease in leukocyte activation and 4-fold decrease in tissue injury. These findings have never been demonstrated in the literature and suggest a novel and non-obvious application of carbon monoxide in the treatment of CS. The use of CORM-3 has demonstrated the protective effects of carbon monoxide in CS.

CORM-3 may be applied to any tibial fracture to decrease the risk of developing CS, and hence the risk of amputation and disability. The military has demonstrated priority in advancing the treatment of CS, as extremity injuries and subsequent amputation are common in soldiers.

Example 4

Comparison Between the Systemic Application of CO-Releasing Molecules (CORM-3) and Inhaled CO in the Severity of Microvascular Dysfunction Due to Compartment Syndrome Animal preparation, intravital video microscopy, compartment syndrome monitoring groups and preparation of CORM-3 were similar to Example 3.

Upon reperfusion, 250 ppm CO in medical air was applied by inhalation, for the duration of the reperfusion interval and IVVM.

Figure 13:
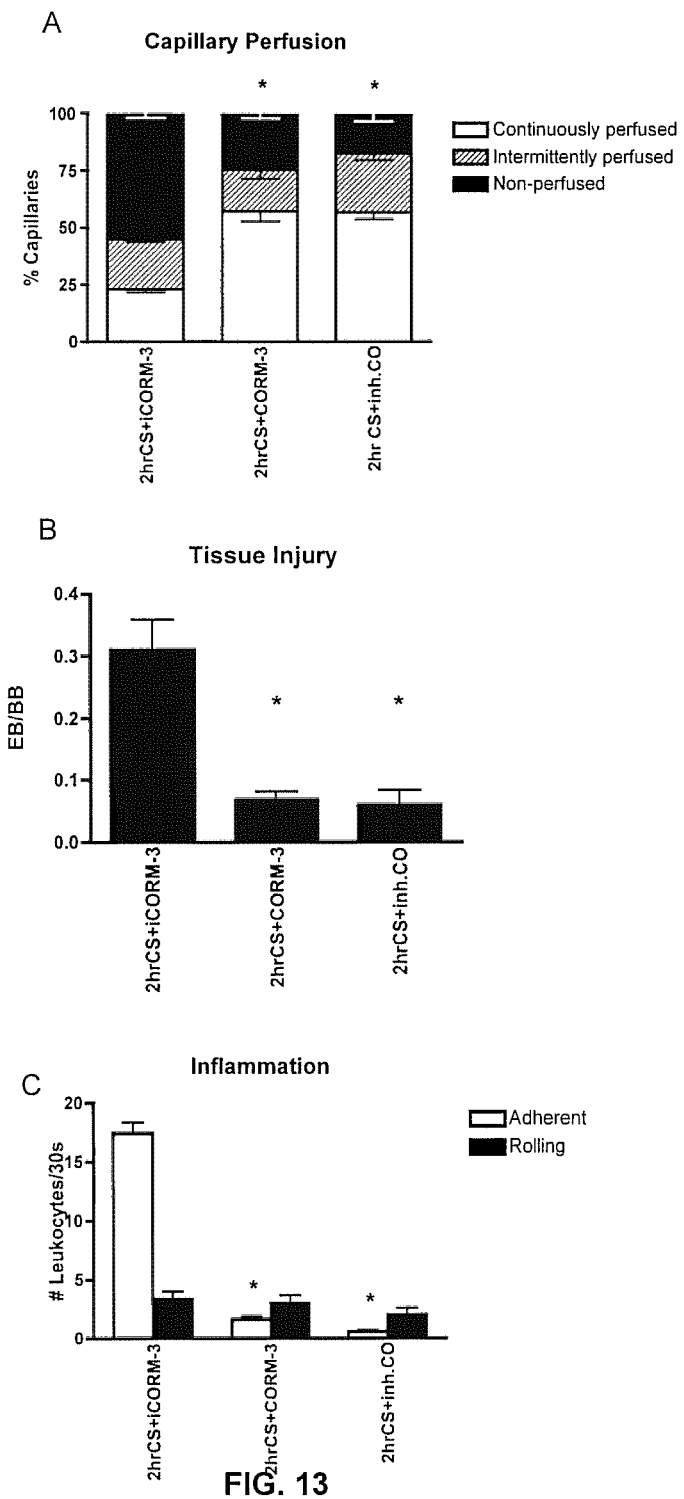
FIG. 13 are graphs showing comparisons between iCORM-3, CORM-3 and inhaled CO in capillary perfusion (panel A), tissue injury (panel B), inflammation (panel C).
Figure 14:
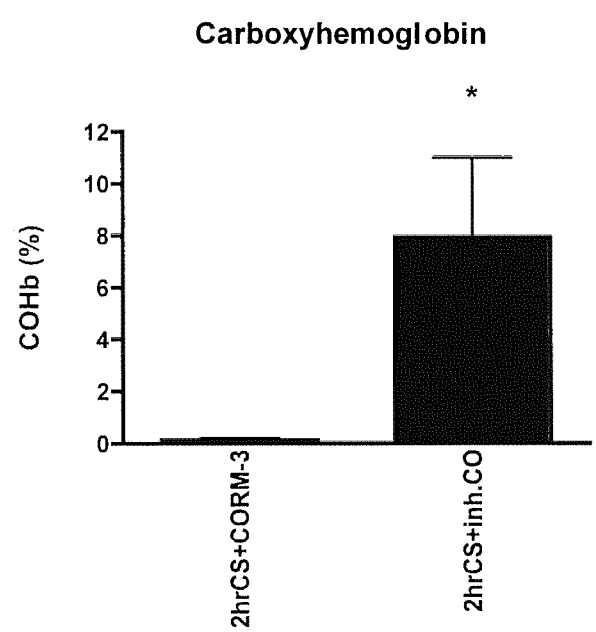
FIG. 14 is a graph showing a comparison between CORM-3 and inhaled CO in carboxyhemoglobin.

Results are shown in FIGS. 13 and 14. As shown in FIGS. 13 and 14, inhaled CO has similar effects as CORM-3 in CS. The use of inhaled CO has demonstrated the protective effects of carbon monoxide in CS.

Example 5

Pig Studies

In order to use CORM-3 in human patients, the substance has to be tested in a large animal model of CS. Pigs were chosen due to their size and similarity to humans.

Following the basic surgical setup (anesthesia, intubation, auricular vein and femoral artery catheterization), the animals undergo 6 hours of elevated intra-compartmental pressure (i.e. CS), followed by fasciotomy and reperfusion. The time interval was chosen in order to closely mimic the condition in human patients. CORM-3 (or iCORM-3), 10 mg/kg of animal is applied prior to fasciotomy. Blood is sampled at various time intervals (baseline, 1 hr CS, 2 hr CS, 3 hr CS, 4 hr CS, 5 hr CS, 6 hr CS/fasciotomy, and every 10-15 min post-fasciotomy, for a total of 20 samples per animal), in order to monitor leukocyte activation and serum TNF-$\alpha$ levels. IVVM is carried out at 3 hours post-fasciotomy.

Results

Figure 15A:
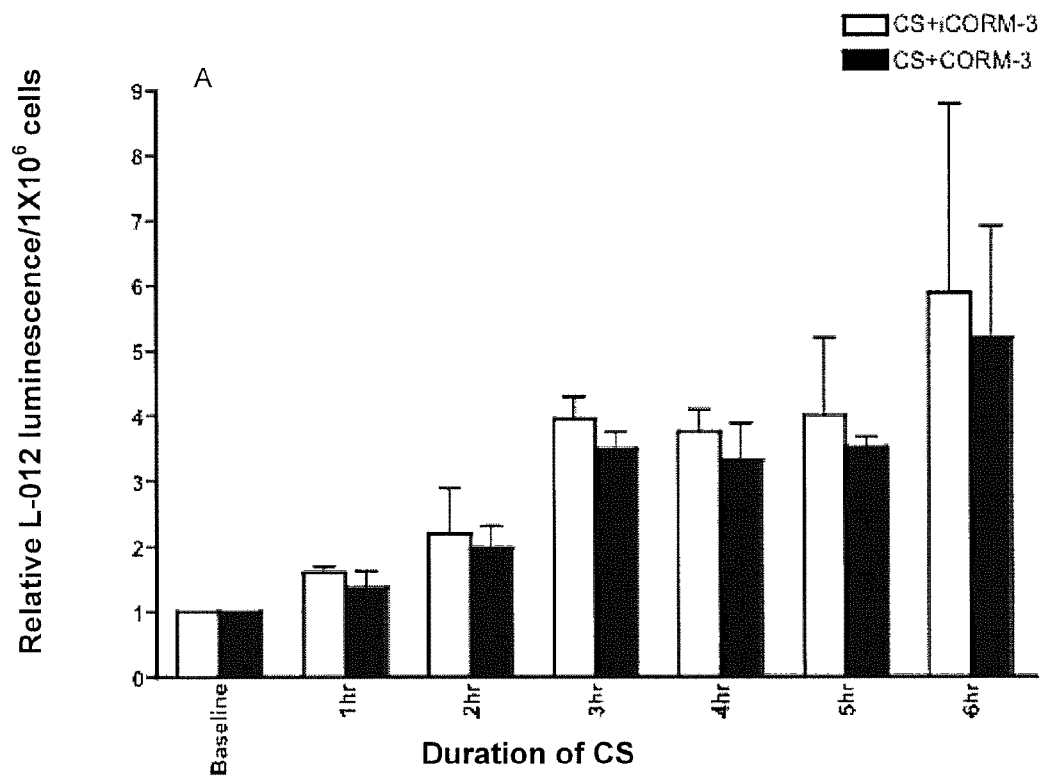
FIG. 15 are graphic representations of leukocyte activation (PMNs) during compartment syndrome (panel A) and post-fasciotomy (panel B) in a porcine model of compartment syndrome. Pigs underwent 6 hours of elevated intra-compartmental pressure (CS), followed by fasciotomy and the injection of CORM-3 (or its inactive form, iCORM-3). Elevation of compartment pressure led to a progressive increase in PMN activation; CORM-3 injection led to a significant decrease in the number of activated PMNs. *$p<0.0001$; N=3 in iCORM-3 group, N=4 in CORM-3 group.
Figure 15B:
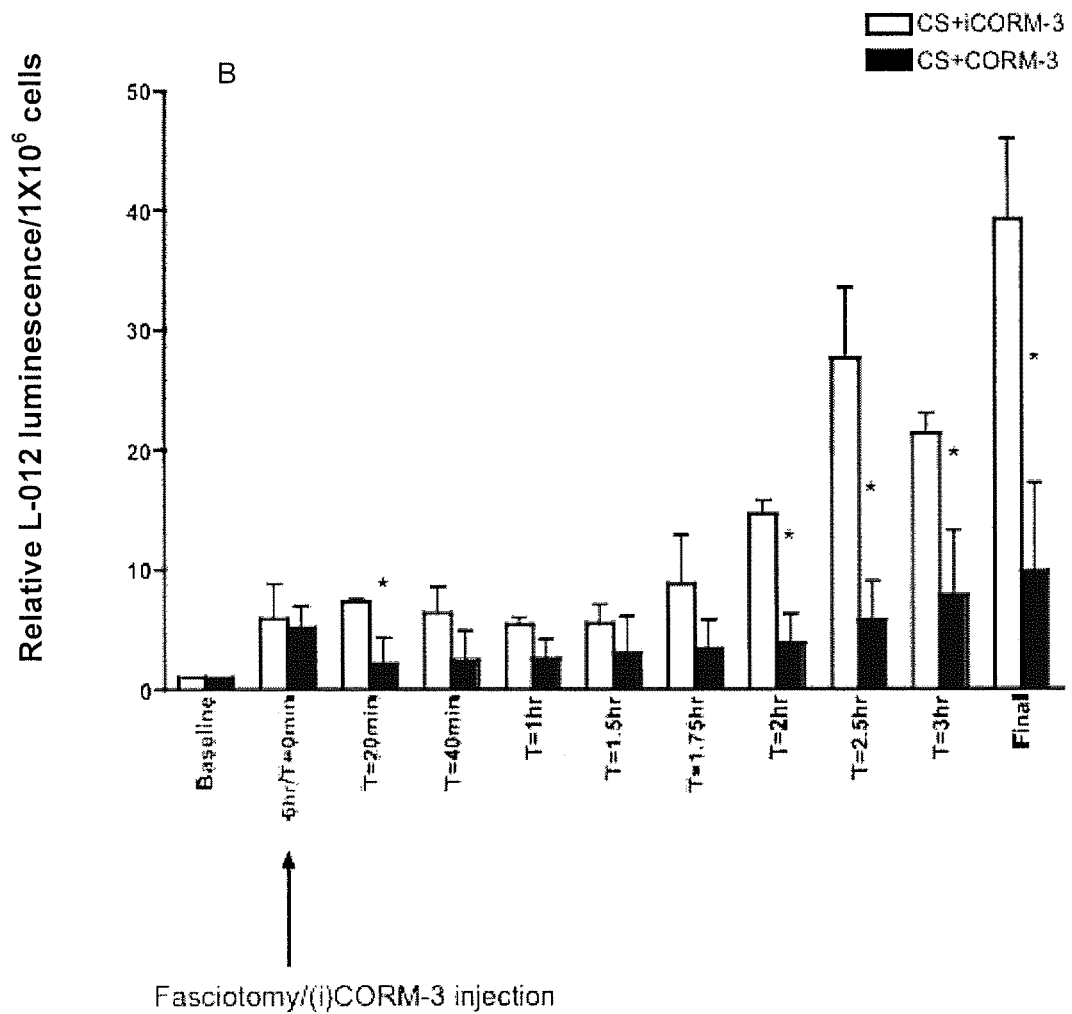
Figure 16:
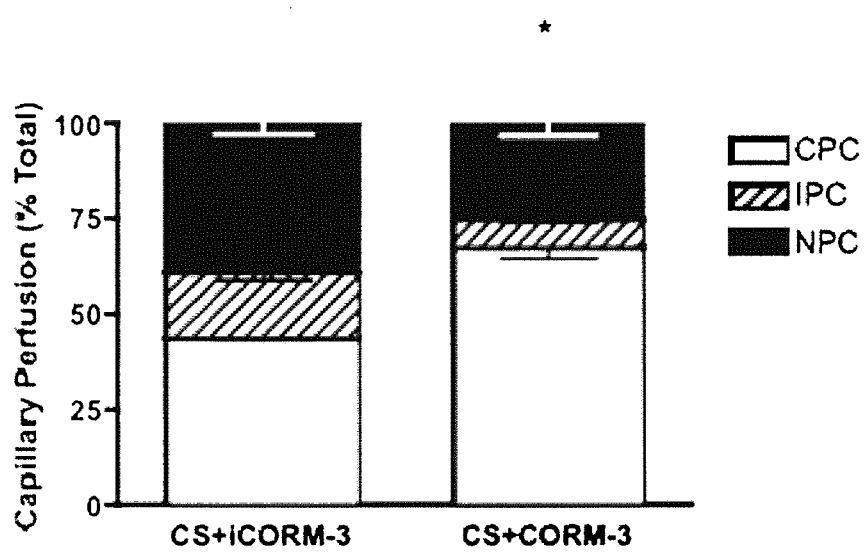
FIG. 16 is a graph illustrating capillary perfusion in porcine model of compartment syndrome. Pigs underwent 6 hours of elevated ICP, followed by fasciotomy, CORM-3/iCORM-3 injection and 3 hours of reperfusion. Capillary perfusion was assessed by intravital video microscopy at 3 hours post-fasciotomy. CORM-3 injection at fasciotomy led to an increase in continuously-perfused capillaries (CPC), and a decrease in intermittently-perfused (IPC) and non-perfused capillaries (NPC). *$p<0.0001$; N=3 in iCORM-3 group, N=4 in CORM-3 group.
Figure 17:
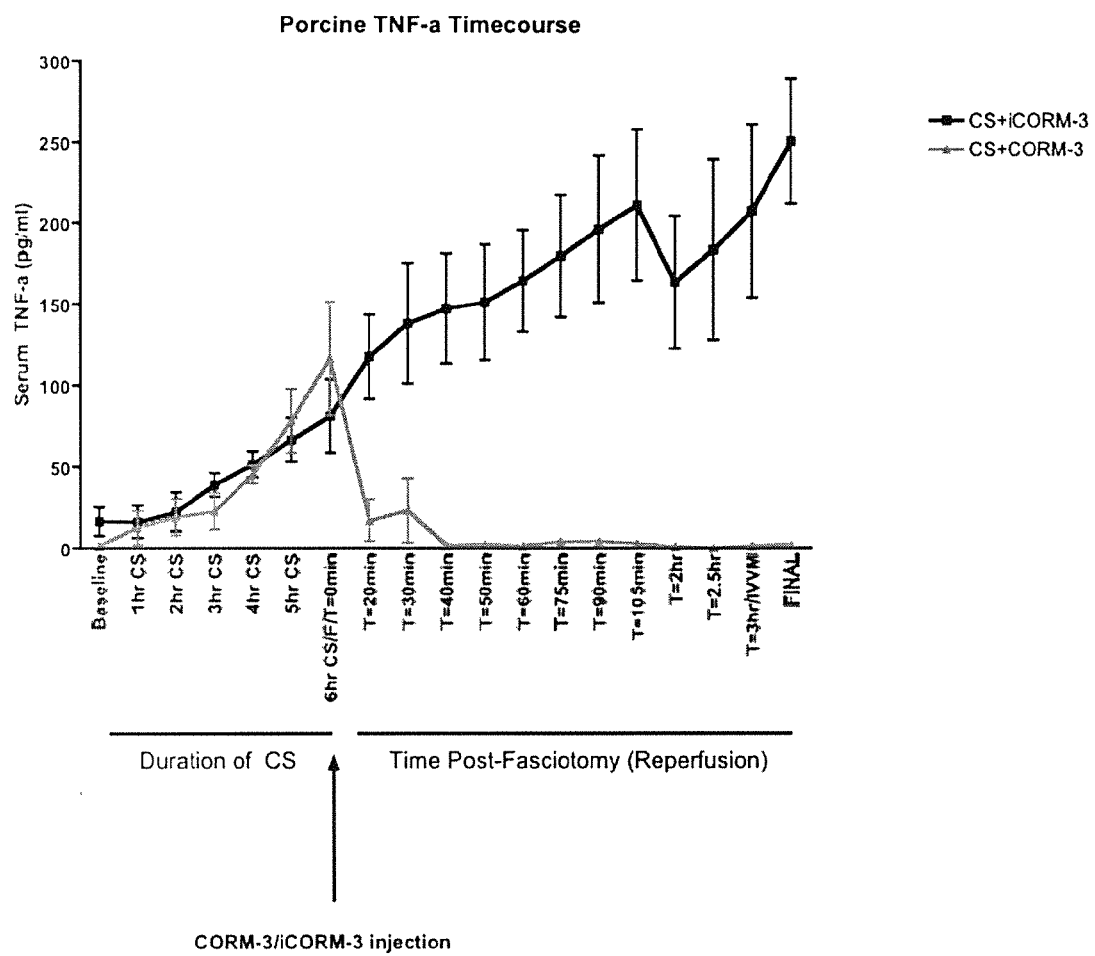
FIG. 17 is a graph illustrating time-course of serum TNF-α in the porcine model of CS. Pigs underwent 6 hours of elevated ICP, followed by fasciotomy, CORM-3/iCORM-3 injection and 3 hours of reperfusion. Capillary perfusion was assessed by intravital video microscopy at 3 hours post-fasciotomy. CORM-3 injection at fasciotomy prevented any TNF-α release associated with post-fasciotomy/reperfusion. $p<0.0001$ from T=20 min onwards; N=3 in iCORM-3 group, N=4 in CORM-3 group.

Results are presented in FIGS. 15-17.

Leukocyte activation (PMNs) during (A) compartment syndrome and (B) post-fasciotomy in the porcine model of CS As shown in FIG. 15A, elevation of intra-compartmental pressure led to a progressive increase in PMN activation. As shown in FIG. 15B, CORM-3 injection led to a significant decrease in the number of activated PMNs (*$p<0.0001$; N=3 in iCORM-3 group, N=4 in CORM-3 group).

Capillary Perfusion in Porcine Model of Compartment Syndrome

As shown in FIG. 16, CORM-3 injection at fasciotomy led to an increase in continuously-perfused capillaries (CPC), and a decrease in intermittently-perfused (IPC) and non-perfused capillaries (NPC). *$p<0.0001$; N=3 in iCORM-3 group, N=4 in CORM-3 group.

Time Course of Serum TNF-$\alpha$ in the Porcine Model of CS

CORM-3 injection at fasciotomy prevented any TNF-$\alpha$ release associated with post-fasciotomy/reperfusion. $p<0.0001$ from T=20 min onwards; N=3 in iCORM-3 group, N=4 in CORM-3 group.

Conclusions

To the knowledge of the Applicants, this is the first study to demonstrate the effects of carbon monoxide in the treatment or relieving of compartment syndrome. The obtained data strongly indicate a potential therapeutic application of CO to patients at risk of developing CS. Carbon monoxide may be administered to patients at risk of developing CS to prevent CS or to extend or prolong the surgical window (in case of delayed fasciotomy), or together with or after fasciotomy to minimize the extent of reperfusion injury.

Example 6

Wistar rats were randomized into three groups: sham (no CS; n=4), CS with inactive CORM-3 (iCORM-3; n=4) and CS plus CORM-3 (n=4; 10 mg/kg IP). Animal preparation and synthesis of CORM-3 were similar to Example 3. In this experiment the animals did not undergo fasciotomy.

Complete inducement of CS occurred at about 180 minutes post induction. The animals were injected at 180 minutes and every 24 hours thereafter.

Quantitative assessment of footfalls and gait in the rats was assessed using CatWalk™, which a system for quantitative assessment of footfalls and gait in rats and mice.

Figure 18:
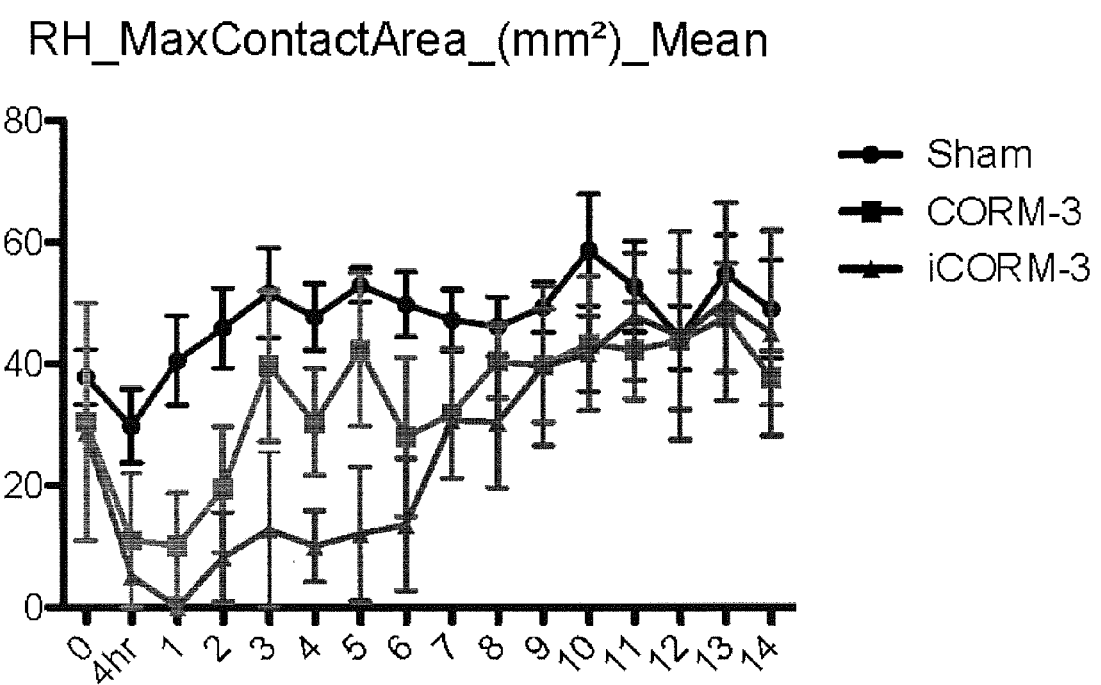
FIG. 18 is a graph illustrating right hind (RH) leg maximum contact area. Max Contact Area is the maximum area of a paw that comes into contact with the glass plate of the CatWalk™ system.
Figure 19:
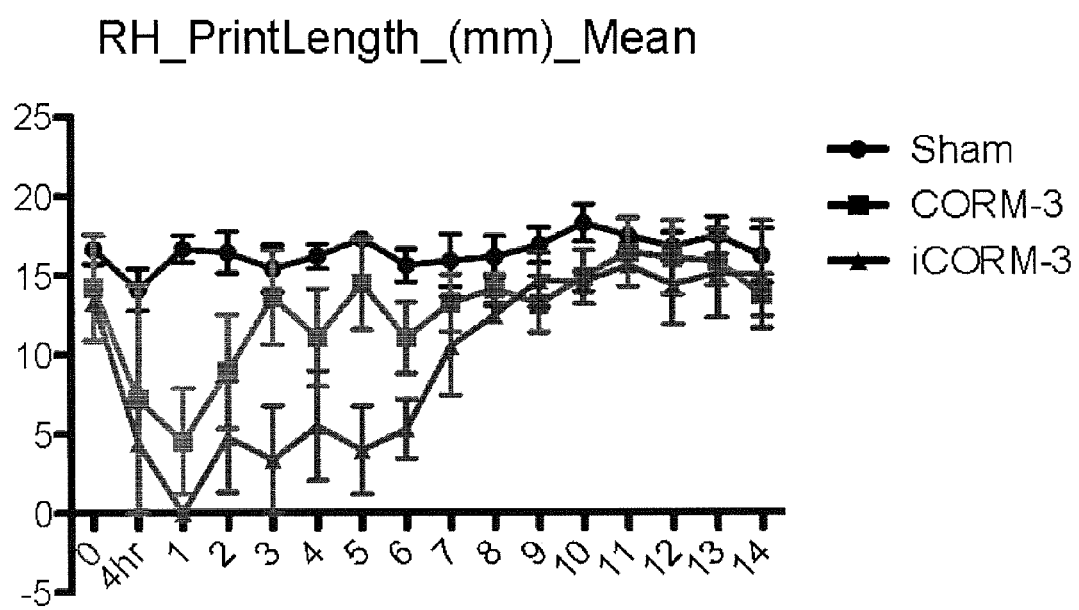
FIG. 19 is a graph illustrating right hind (RH) leg print length mean, length on the horizontal direction of the complete print (sum of all contacts within the glass plate of the CatWalk™ system).

Results static and dynamic gait parameters showing functional effect of multi dose CORM-3/iCORM-3 post 180 min CS. are shown FIGS. 18 and 19. Administration of CORM-3 significantly improved the functional parameters relative to iCORM-3. CO-RM-3 demonstrates an improvement in weight bearing parameters in the CO-RM-3 treated rats.

REFERENCES

1. Matsen, F. A., 3rd. Compartmental syndromes. *Hospital Practice* 15, 113-117 (1980).

2. Mubarak, S. J., Owen, C. A., Hargens, A. R., et al. Acute compartment syndromes: diagnosis and treatment with the aid of the wick catheter. *The Journal of Bone and Joint Surgery. American volume* 60, 1091-1095 (1978).
3. Whitesides, T. E., Haney, T. C., Morimoto, K. et al. Tissue pressure measurements as a determinant for the need of fasciotomy. *Clinical Orthopaedics and Related Research*, 43-51 (1975).
4. Matsen, F. A., 3rd. Compartmental syndrome. An unified concept. *Clinical Orthopaedics and Related Research*, 8-14 (1975).
5. Rorabeck, C. H. & Clarke, K. M. The pathophysiology of the anterior tibial compartment syndrome: an experimental investigation. *The Journal of Trauma* 18, 299-304 (1978).
6. Hartsock, L. A., O'Farrell, D., Seaber, A. V. et al. Effect of increased compartment pressure on the microcirculation of skeletal muscle. *Microsurgery* 18, 67-71 (1998).
7. Matsen, F. A., 3rd, Winquist, R. A. & Krugmire, R. B., Jr. Diagnosis and management of compartmental syndromes. *The Journal of Bone and Joint Surgery. American Volume* 62, 286-291 (1980).
8. Sheridan, G. W. & Matsen, F. A. An animal model of the compartmental syndrome. *Clinical Orthopaedics and Related Research*, 36-42 (1975).
9. Lawendy, A. R., Bihari, A., Sanders, D. W., et al. Compartment syndrome-induced microvascular dysfunction: an experimental rodent model. *Canadian Journal of Surgery* 54, 194-200 (2011).
10. Sadasivan, K. K., Carden, D. L., Moore, M. B., et al. Neutrophil mediated microvascular injury in acute, experimental compartment syndrome. *Clinical Orthopaedics and Related Research*, 206-215 (1997).
11. Kalns, J., Cox, J., Baskin, J., et al. Threshold model for extremity compartment syndrome in swine. *Journal of Surgical Research* 167, e13-19 (2011).
12. Ott, M. C., Scott, J. R., Bihari, A., et al. Inhalation of carbon monoxide prevents liver injury and inflammation following hind limb ischemia/reperfusion. *The FASEB Journal* 19, 106-108 (2005).
13. Scott, J. R., Cukiernik, M. A., Ott, M. C., et al. Low-dose inhaled carbon monoxide attenuates the remote intestinal inflammatory response elicited by hindlimb ischemic-reperfusion. *American Journal of Physiology. Gastrointestinal and Liver Physiology* 296, G9-G14 (2009).
14. Hegazi, R. A., Rao, K. N., Mayle, A., et al. Carbon monoxide ameliorates chronic murine colitis through a heme oxygenase 1-dependent pathway. *Journal of Experimental Medicine* 202, 1703-1713 (2005).
15. Nakao, A., Kimizuka, K., Stolz, D. B., et al. Carbon monoxide inhalation protects rat intestinal grafts from ischemia/reperfusion injury. *American Journal of Pathology* 163, 1587-1598 (2003).
16. Mazzola, S., Forni, M., Albertini, M., et al. Carbon monoxide pretreatment prevents respiratory derangement and ameliorates hyperacute endotoxic shock in pigs. *FASEB Journal* 19, 2045-2047 (2005).
17. Motterlini, R. & Otterbein, L. E. The therapeutic potential of carbon monoxide. *Nature Review Drug Discovery* 9, 728-743 (2010).
18. Motterlini, R. Carbon monoxide-releasing molecules (CO-RMs): vasodilatory, anti-ischaemic and anti-inflammatory activities. *Biochemical Society Transactions* 35, 1142-1146 (2007).
19. Motterlini, R., Clark, J. E., Foresti, R., et al. Carbon monoxide-releasing molecules: characterization of biochemical and vascular activities. *Circulation Research* 90, E17-24 (2002).
20. Cepinskas, G., Katada, K., Bihari, A., et al. Carbon monoxide liberated from carbon monoxide-releasing molecule CORM-2 attenuates inflammation in the liver of septic mice. *American Journal of Physiology. Gastrointestinal and Liver Physiology* 294, G184-191 (2008).
21. Katada, K., Bihari, A., Mizuguchi, S., et al. Carbon monoxide liberated from CO-releasing molecule (CORM-2) attenuates ischemia/reperfusion (I/R)-induced inflammation in the small intestine. *Inflammation* 33, 92-100 (2010).
22. Mizuguchi, S., Stephen, J., Bihari, A., et al. CORM-3-derived CO modulates polymorphonuclear leukocyte migration across the vascular endothelium by reducing levels of cell surface-bound elastase. *American journal of physiology. Heart and Circulatory Physiology* 297, H920-929 (2009).
23. Clark, J. E., Naughton, P., Shurey, S., et al. Cardioprotective actions by a water-soluble carbon monoxide-releasing molecule. *Circulation Research* 93, e2-8 (2003).
24. Olson, S. A. & Glasgow, R. R. Acute compartment syndrome in lower extremity musculoskeletal trauma. *Journal of American Academy of Orthopaedic Surgeons* 13, 436-444 (2005).
25. Santos-Silva, T., Mukhopadhyay, A., Seixas, J. D., et al. CORM-3 reactivity toward proteins: the crystal structure of a Ru(II) dicarbonyl-lysozyme complex. *Journal of American Chemical Society* 133, 1192-1195 (2011).
26. Vadori, M., Seveso M., Besenzon, F., et al. In vitro and in vivo effects of the carbon monoxide-releasing molecule, CORM-3, in the xenogeneic pig-to-primate context. *Xenotransplantation* 16, 99-114 (2009).
27. Katada, K., Bihari, A., Badhwar, A., et al. Hindlimb ischemia/reperfusion-induced remote injury to the small intestine: role of inducible nitric-oxide synthase-derived nitric oxide. *The Journal of Pharmacology and Experimental Therapeutics* 329, 919-927 (2009).
28. Otterbein, L. E. The evolution of carbon monoxide into medicine. *Respiratory Care* 54, 925-932 (2009).
29. Forbes, T. L., Carson, M., Harris, K. A., et al. Skeletal muscle injury induced by ischemia-reperfusion. *Canadian Journal of Surgery* 38, 56-63 (1995).
30. Gute, D. C., Ishida, T., Yarimizu, K., et al. Inflammatory responses to ischemia and reperfusion in skeletal muscle. *Molecular and Cellular Biochemistry* 179, 169-187 (1998).
31. Kurose, I., Anderson, D. C., Miyasaka, M., et al. Molecular determinants of reperfusion-induced leukocyte adhesion and vascular protein leakage. *Circulation Research* 74, 336-343 (1994).
32. Forbes, T. L., Harris, K. A., Jamieson, W. G., et al. Leukocyte activity and tissue injury following ischemia-reperfusion in skeletal muscle. *Microvascular Research* 51, 275-287 (1996).
33. Mizuguchi, S., Capretta, A., Suehiro, S., et al. Carbon monoxide-releasing molecule CORM-3 suppresses vascular endothelial cell SOD-1/SOD-2 activity while up-regulating the cell surface levels of SOD-3 in a heparin-dependent manner. *Free Radical Biology & Medicine* 49, 1534-1541 (2010).
34. Song, H., Bergstrasser, C., Rafat, N., et al. The carbon monoxide releasing molecule (CORM-3) inhibits expression of vascular cell adhesion molecule-1 and E-selectin independently of haem oxygenase-1 expression. *British Journal of Pharmacology* 157, 769-780 (2009).
35. Bergstraesser, C., Hoeger, S., Song, H., et al. Inhibition of VCAM-1 expression in endothelial cells by CORM-3: the role of the ubiquitin-proteasome system, p38, and mitochondrial respiration. *Free Radical Biology and Medicine* 52, 794-802 (2012).
36. Ley, K., Laudanna, C., Cybulsky, M. I., et al. Getting to the site of inflammation: the leukocyte adhesion cascade updated. *Nature Review Immunology* 7, 678-689 (2007).
37. Lancel, S., Hassoun, S. M., Favory, R., et al. Carbon monoxide rescues mice from lethal sepsis by supporting mitochondrial energetic metabolism and activating mitochondrial biogenesis. *Journal of Pharmacology and Experimental Therapeutics* 329, 641-648 (2009).
38. Foresti, R., Hammad, J., Clark, J. E., et al. Vasoactive properties of CORM-3, a novel water-soluble carbon monoxide-releasing molecule. *British Journal of Pharmacology* 142, 453-460 (2004).
39. Sabido F, Milazzo V J, Hobson R W, 2nd and Duran W N (1994). Skeletal muscle ischemia-reperfusion injury: a review of endothelial cell-leukocyte interactions. J Invest Surg 7(1): 39-47.
40. Kurose I, Argenbright L W, Wolf R, Lianxi L and Granger D N (1997). Ischemia/reperfusion-induced microvascular dysfunction: role of oxidants and lipid mediators. Am J Physiol 272(6 Pt 2): H2976-2982.
41. Seddon H J (1966). Volkmann's ischaemia in the lower limb. J Bone Joint Surg Br 48(4): 627-636.
42. Potter R F, Dietrich H H, Tyml K, Ellis C G, Cronkwright J, Groom A C (1993). Ischemia-reperfusion induced microvascular dysfunction in skeletal muscle: application of intravital video microscopy. Int J Microcirc Clin Exp. 13: 173-186.
43. Tyml K, Budreau C H (1991). A new preparation of rat extensor digitorum longus muscle for intravital investigation of the microcirculation. Int J Microcirc Clin Exp. 10(4): 335-343.
44. Potter R F, Peters G, Carson M, Forbes T, Ellis C G, Harris K A, DeRose G, Jamieson W G (1995). Measurement of tissue viability using intravital microscopy and fluorescent nuclear dyes. J Surg Res. 59(5): 521-526.
45. Brock R W, Carson M W, Harris K A, Potter R F (1999). Microcirculatory perfusion deficits are not essential for remote parenchymal injury within the liver. Am J Physiol. 277(1 Pt 1): G55-60.
46. Campbell J J, Hedrick J, Zlotnik A, Siani M A, Thompson D A, Butcher E C (1998). Chemokines and the arrest of the lymphocytes rolling under flow conditions. Science 279: 381-384.
47. Schlag G, Harris K A, Potter R F (2001). Role of leukocyte accumulation and oxygen radicals in ischemia-reperfusion-induced injury in skeletal muscle. Am J Physio Heart Circ Physiol. 280(4): H1716-21.
48. Heppenstall R B, Scott R, Sapega, A, Park Y S, Chance B (1986). A comparative study of the tolerance of skeletal muscle to ischemia. Tourniquet application compared with acute compartment syndrome. J Bone and Joint Surg. 68-A: 820-823.
49. Matsen F A III, Mayo K A, Krugmire R B, Sheridan G W, Kraft G H (1977). A model compartmental syndrome in man with particular reference to the quantification of nerve function. J Bone and Joint Surg. 59-A: 648-653.
50. Sheridan G W, Matsen F A, Krugmire R B Jr (1977). Further investigation on the pathophysiology of the compartment syndrome. Clin Orthop. 123: 266-267.
51. Conrad M F, Stone D H, Albadawi H, Hua H T, Entabi F, Stoner M C, Watkins M T (2005). Local inflammatory and thrombotic responses differ in a murine model of partial and complete hindlimb ischemia/reperfusion. Surgery 138: 375-81.

The above disclosure generally describes the present invention. Changes in form and substitution of equivalents are contemplated as circumstances may suggest or render expedient. Although specific terms have been employed herein, such terms are intended in a descriptive sense and not for purposes of limitation. It is to be understood that the present invention is not limited to the embodiments described above, but encompasses any and all embodiments within the scope of the following claims.

Therefore what is claimed is:

1. A method of treating compartment syndrome in a patient having compartment syndrome, the method comprising administering to the patient a therapeutically effective amount of carbon monoxide (CO).

2. The method of claim 1, wherein the CO is provided as a gaseous composition comprising CO and at least one more gaseous molecule.

3. The method of claim 1, wherein the CO is provided as a liquid composition comprising the CO and a liquid solution suitable for administration to the patient.

4. The method of claim 1, wherein the CO is provided in a carbon monoxide releasing molecule (CORM).

5. The method of claim 4, wherein the CORM is CORM-3 (tricarbonylchloro-glycinate-ruthenium (II)).

6. The method of claim 5, wherein the CORM is provided as a single dose or multiple dosages, each dose comprising about 10 mg of CORM per kg of the patient.

7. The method of claim 4, wherein the CORM is selected from the group consisting of tricarbonyldichloro ruthenium (II) dimer, sodium boranocarbonate, dimanganese decacarbonyl, and iron pentacarbonyl.

8. The method of claim 1, wherein the CO is provided from about 50 ppm to about 500 ppm.

9. The method of claim 1, wherein the CO is provided at a concentration of between about 0.0001% to about 0.25% by weight of the patient.

10. The method of claim 1, wherein the CO is administered before, during or after the patient undergoing fasciotomy.

11. The method of claim 1, wherein the compartment syndrome is in a limb of the patient.

12. A method for treating elevated pressure in a closed osseofascial compartment comprising administering to a patient carbon monoxide (CO) in an amount sufficient to decrease pressure in the closed osseofascial compartment.

13. The method of claim 12 wherein the CO is provided as a gaseous composition comprising CO and at least one more gaseous molecule.

14. The method of claim 12, wherein the CO is provided as a liquid composition comprising the CO and a liquid solution suitable for administration to the patient.

15. The method of claim 12, wherein the CO is provided in a carbon monoxide releasing molecule (CORM).

16. The method of claim 15, wherein the CORM is CORM-3 (tricarbonylchloro-glycinate-ruthenium (II)).

17. The method of claim 16, wherein the CORM is provided as a single dose or multiple dosages comprising about 10 mg CORM per Kg of patient.

18. The method of claim 15, wherein the CORM is selected from the group consisting of tricarbonyldichloro ruthenium (II) dimer, sodium boranocarbonate, dimanganese decacarbonyl, and iron pentacarbonyl.

19. The method of claim 12, wherein the CO is provided from about 50 ppm to about 500 ppm.

20. The method of claim 12, wherein the CO is provided at a concentration of between about 0.0001% to about 0.25% by weight of the patient.

21. The method of claim 12, wherein the elevated compartment pressure is in a limb of the patient.

22. A method of treating a subject who has experienced limb trauma and is at risk of developing acute limb compartment syndrome, the method comprising administering to the subject a therapeutically effective amount of carbon monoxide (CO).

23. The method of claim 22, wherein the CO is provided as a gaseous composition comprising CO and at least one more gaseous molecule.

24. The method of claim 22, wherein the CO is provided as a liquid composition comprising the CO and a liquid solution suitable for administration to the subject.

25. The method of claim 22, wherein the CO is provided in a carbon monoxide releasing molecule (CORM).

26. The method of claim 25, wherein the CORM is tricarbonylchloro-glycinate-ruthenium (II).

27. The method of claim 26, wherein the CORM is provided as a single does or multiple dosages comprising about 10 mg of CORM per Kg of the subject.

28. The method of claim 25, wherein the CORM is selected from the group consisting of tricarbonyldichloro ruthenium (II) dimer, sodium boranocarbonate, dimanganese decacarbonyl, and iron pentacarbonyl.

29. The method of claim 22, wherein the CO is provided from about 50 ppm to about 500 ppm.

30. The method of claim 22, wherein the CO is provided at a concentration of between about 0.0001% to about 0.25% by weight of the subject.

\* \* \* \* \*